(12) United States Patent
Cloutier et al.

(10) Patent No.: US 11,116,500 B2
(45) Date of Patent: Sep. 14, 2021

(54) SURGICAL FASTENER APPLYING DEVICE, KITS AND METHODS FOR ENDOSCOPIC PROCEDURES

(71) Applicant: Covidien LP, Mansfield, MA (US)

(72) Inventors: Kayla N. Cloutier, New Haven, CT (US); Jin Yong, Watertown, CT (US); Michael J. Kolb, Southington, CT (US); Kevin S. Sniffin, Roxbury, CT (US)

(73) Assignee: COVIDIEN LP, Mansfield, MA (US)

( * ) Notice: Subject to any disclaimer, the term of this patent is extended or adjusted under 35 U.S.C. 154(b) by 238 days.

(21) Appl. No.: 16/367,916

(22) Filed: Mar. 28, 2019

(65) Prior Publication Data

US 2020/0000460 A1 Jan. 2, 2020

Related U.S. Application Data

(60) Provisional application No. 62/691,137, filed on Jun. 28, 2018.

(51) Int. Cl.
*A61B 17/068* (2006.01)
*A61B 17/00* (2006.01)
(Continued)

(52) U.S. Cl.
CPC ...... *A61B 17/068* (2013.01); *A61B 17/00234* (2013.01); *A61B 17/1285* (2013.01);
(Continued)

(58) Field of Classification Search
CPC ............ A61B 17/068; A61B 17/00234; A61B 17/1285; A61B 17/8875;
(Continued)

(56) References Cited

U.S. PATENT DOCUMENTS

| 3,596,528 A | 8/1971 | Dittrich et al. |
| 3,866,510 A | 2/1975 | Eibes et al. |

(Continued)

FOREIGN PATENT DOCUMENTS

| EP | 0374088 A1 | 6/1990 |
| JP | 09149906 | 6/1997 |
| WO | 2016011594 A1 | 1/2016 |

OTHER PUBLICATIONS

Extended European Search Report corresponding to EP 14 15 8946.5, completed Jun. 20, 2014 and dated Jul. 8, 2014;(9 pp).

(Continued)

*Primary Examiner* — Shaun L David
*Assistant Examiner* — Joshua T Hicks

(57) ABSTRACT

A surgical device is provided and includes a handle housing, an endoscopic assembly, and a follower assembly. The endoscopic assembly extends distally from the handle housing and includes an inner tube defining a longitudinal axis. The inner tube includes a distal portion defining a pair of opposed tines. The endoscopic assembly is configured to support a plurality of anchors at least partially therein. The follower assembly is disposed at least partially within the inner tube at a location proximal of the plurality of anchors, and includes a head and a shaft. A portion of the head is disposed between the pair of opposed tines. Actuation of the endoscopic surgical device causes rotation of the inner tube about the longitudinal axis relative to the handle housing, and causes distal advancement of the follower assembly relative to the inner tube.

20 Claims, 13 Drawing Sheets

(51) Int. Cl.
   *A61B 17/128* (2006.01)
   *A61B 17/88* (2006.01)
   *A61F 2/00* (2006.01)
(52) U.S. Cl.
   CPC ........ *A61B 17/8875* (2013.01); *A61F 2/0063* (2013.01); *A61F 2002/0072* (2013.01)
(58) Field of Classification Search
   CPC .. A61B 2017/0046; A61B 2017/00407; A61B 2017/0648; A61B 17/0469; A61F 2/0063; A61F 2002/0072
   See application file for complete search history.

(56) References Cited

U.S. PATENT DOCUMENTS

| | | |
|---|---|---|
| 4,350,491 A | 9/1982 | Steuer |
| 4,730,726 A | 3/1988 | Holzwarth |
| 4,884,572 A | 12/1989 | Bays et al. |
| 5,085,661 A | 2/1992 | Moss |
| 5,144,942 A | 9/1992 | Decarie et al. |
| 5,156,267 A | 10/1992 | Yates, Jr. et al. |
| 5,171,247 A | 12/1992 | Hughett et al. |
| 5,171,249 A | 12/1992 | Stefanchik et al. |
| 5,176,306 A | 1/1993 | Heimerl et al. |
| 5,207,697 A | 5/1993 | Carusillo et al. |
| 5,228,256 A | 7/1993 | Dreveny |
| 5,236,563 A | 8/1993 | Loh |
| 5,246,441 A | 9/1993 | Ross et al. |
| 5,246,450 A | 9/1993 | Thornton et al. |
| 5,312,023 A | 5/1994 | Green et al. |
| 5,330,487 A | 7/1994 | Thornton et al. |
| 5,344,061 A | 9/1994 | Crainich |
| 5,353,929 A | 10/1994 | Foster |
| 5,356,064 A | 10/1994 | Green et al. |
| 5,381,896 A | 1/1995 | Simons |
| 5,382,254 A | 1/1995 | McGarry et al. |
| 5,398,861 A | 3/1995 | Green |
| 5,403,327 A | 4/1995 | Thornton et al. |
| 5,407,070 A | 4/1995 | Bascos et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Alesi et al. |
| 5,474,567 A | 12/1995 | Stefanchik et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,607,436 A | 3/1997 | Pratt et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,704,534 A | 1/1998 | Huitema et al. |
| 5,709,692 A | 1/1998 | Mollenauer et al. |
| 5,728,116 A | 3/1998 | Rosenman |
| 5,730,744 A | 3/1998 | Justin et al. |
| 5,732,806 A | 3/1998 | Foshee et al. |
| 5,735,854 A | 4/1998 | Caron et al. |
| 5,741,268 A | 4/1998 | Schutz |
| 5,762,255 A | 6/1998 | Chrisman et al. |
| 5,782,844 A | 7/1998 | Yoon et al. |
| 5,792,165 A | 8/1998 | Klieman et al. |
| 5,810,882 A | 9/1998 | Bolduc et al. |
| 5,824,008 A | 10/1998 | Bolduc et al. |
| 5,830,221 A | 11/1998 | Stein et al. |
| 5,843,087 A | 12/1998 | Jensen et al. |
| 5,897,564 A | 4/1999 | Schulze et al. |
| 5,904,693 A | 5/1999 | Dicesare et al. |
| 5,910,105 A | 6/1999 | Swain et al. |
| 5,911,722 A | 6/1999 | Adler et al. |
| 5,928,244 A | 7/1999 | Tovey et al. |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A | 9/1999 | Viola et al. |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A | 8/2000 | Sugai et al. |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan et al. |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,757 B1 | 6/2002 | Moore, III et al. |
| 6,402,780 B2 | 6/2002 | Williamson, IV et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,450,391 B1 | 9/2002 | Kayan et al. |
| 6,457,625 B1 | 10/2002 | Tormala et al. |
| 6,551,333 B2 | 4/2003 | Kuhns et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze et al. |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,070,601 B2 | 7/2006 | Culbert et al. |
| 7,122,028 B2 | 10/2006 | Looper et al. |
| 7,128,754 B2 | 10/2006 | Bolduc |
| 7,147,657 B2 | 12/2006 | Chiang et al. |

(56) References Cited

U.S. PATENT DOCUMENTS

| | | |
|---|---|---|
| 7,204,847 B1 | 4/2007 | Gambale |
| 7,261,716 B2 | 8/2007 | Strobel et al. |
| 7,357,287 B2 | 4/2008 | Shelton, IV et al. |
| 7,380,696 B2 | 6/2008 | Shelton, IV et al. |
| 7,404,508 B2 | 7/2008 | Smith et al. |
| 7,410,086 B2 | 8/2008 | Ortiz et al. |
| 7,434,717 B2 | 10/2008 | Shelton, IV et al. |
| 7,461,574 B2 | 12/2008 | Lewis et al. |
| 7,491,232 B2 | 2/2009 | Bolduc et al. |
| 7,544,198 B2 | 6/2009 | Parodi |
| 7,591,842 B2 | 9/2009 | Parodi |
| 7,611,521 B2 | 11/2009 | Lubbers et al. |
| 7,637,905 B2 | 12/2009 | Saadat et al. |
| 7,637,932 B2 | 12/2009 | Bolduc et al. |
| 7,670,362 B2 | 3/2010 | Zergiebel |
| 7,740,159 B2 | 6/2010 | Shelton, IV et al. |
| 7,758,612 B2 | 7/2010 | Shipp |
| 7,811,312 B2 | 10/2010 | Stevens et al. |
| 7,819,884 B2 | 10/2010 | Lee et al. |
| 7,823,267 B2 | 11/2010 | Bolduc |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,913,892 B2 | 3/2011 | Cole et al. |
| 7,922,061 B2 | 4/2011 | Shelton, IV et al. |
| 7,922,063 B2 | 4/2011 | Zemlok et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,006,365 B2 | 8/2011 | Levin et al. |
| 8,034,076 B2 | 10/2011 | Criscuolo et al. |
| 8,062,306 B2 | 11/2011 | Nobis et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,152,820 B2 | 4/2012 | Mohamed et al. |
| 8,181,840 B2 | 5/2012 | Milliman |
| 8,216,254 B2 | 7/2012 | McLean et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,333,776 B2 | 12/2012 | Cheng et al. |
| 8,343,176 B2 | 1/2013 | Criscuolo et al. |
| 8,343,184 B2 | 1/2013 | Blier |
| 8,377,044 B2 | 2/2013 | Coe et al. |
| 8,382,773 B2 | 2/2013 | Whitfield et al. |
| 8,382,778 B2 | 2/2013 | Criscuolo et al. |
| 8,414,627 B2 | 4/2013 | Corradi et al. |
| 8,424,740 B2 | 4/2013 | Shelton, IV et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,603,135 B2 | 12/2013 | Mueller |
| 8,672,209 B2 | 3/2014 | Crainich |
| 8,684,247 B2 | 4/2014 | Scirica et al. |
| 8,685,044 B2 | 4/2014 | Bolduc et al. |
| 8,690,889 B2 | 4/2014 | Colesanti et al. |
| 8,690,897 B2 | 4/2014 | Bolduc |
| 8,728,098 B2 | 5/2014 | Daniel et al. |
| 8,728,099 B2 | 5/2014 | Cohn et al. |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,894,669 B2 | 11/2014 | Nering et al. |
| 8,920,439 B2 | 12/2014 | Cardinale et al. |
| 8,926,637 B2 | 1/2015 | Zergiebel |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,345,462 B2 | 5/2016 | Weitzner et al. |
| 9,351,728 B2 * | 5/2016 | Sniffin ................. A61B 17/068 |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,231 B2 | 6/2016 | Wenchell |
| 9,364,274 B2 | 6/2016 | Zergiebel |
| 9,386,983 B2 | 7/2016 | Swensgard et al. |
| 9,402,623 B2 | 8/2016 | Kayan |
| 9,445,814 B2 | 9/2016 | Ranucci et al. |
| 9,486,218 B2 | 11/2016 | Criscuolo et al. |
| 9,526,498 B2 | 12/2016 | Reed |
| 9,615,830 B2 | 4/2017 | Ranucci et al. |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 9,783,329 B2 | 10/2017 | Sniffin et al. |
| 9,788,833 B2 | 10/2017 | Zergiebel et al. |
| 9,801,633 B2 | 10/2017 | Sholev et al. |
| 9,867,620 B2 | 1/2018 | Fischvogt et al. |
| 9,987,010 B2 | 6/2018 | Zergiebel |
| 10,070,860 B2 | 9/2018 | Zergiebel |
| 2003/0009441 A1 | 1/2003 | Holsten et al. |
| 2003/0114839 A1 | 6/2003 | Looper et al. |
| 2004/0092937 A1 | 5/2004 | Criscuolo et al. |
| 2005/0222665 A1 | 10/2005 | Aranyi |
| 2006/0129152 A1 | 6/2006 | Shipp |
| 2006/0129154 A1 | 6/2006 | Shipp |
| 2007/0038220 A1 | 2/2007 | Shipp |
| 2007/0088390 A1 | 4/2007 | Paz et al. |
| 2007/0106317 A1 | 5/2007 | Shelton et al. |
| 2007/0162030 A1 | 7/2007 | Aranyi et al. |
| 2008/0086154 A1 | 4/2008 | Taylor et al. |
| 2008/0097523 A1 | 4/2008 | Bolduc et al. |
| 2008/0277445 A1 | 11/2008 | Zergiebel et al. |
| 2008/0312687 A1 | 12/2008 | Blier |
| 2009/0112234 A1 | 4/2009 | Crainich et al. |
| 2009/0118776 A1 | 5/2009 | Kelsch et al. |
| 2009/0188965 A1 | 7/2009 | Levin et al. |
| 2010/0270354 A1 | 10/2010 | Rimer et al. |
| 2011/0022065 A1 | 1/2011 | Shipp |
| 2011/0071578 A1 * | 3/2011 | Colesanti ............. A61B 17/064 606/305 |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2014/0005678 A1 | 1/2014 | Shelton, IV et al. |
| 2014/0014707 A1 | 1/2014 | Onukuri et al. |
| 2014/0200587 A1 | 7/2014 | Pompee et al. |
| 2014/0243855 A1 * | 8/2014 | Sholev .................. A61B 17/10 606/139 |
| 2014/0276972 A1 * | 9/2014 | Abuzaina ............. A61B 17/064 606/143 |
| 2015/0032130 A1 | 1/2015 | Russo |
| 2015/0133970 A1 | 5/2015 | Ranucci et al. |
| 2015/0327859 A1 | 11/2015 | Bolduc |
| 2016/0007991 A1 | 1/2016 | Bolduc |
| 2016/0007996 A1 | 1/2016 | Bolduc |
| 2016/0074034 A1 | 3/2016 | Shipp |
| 2016/0166255 A1 | 6/2016 | Fischvogt |
| 2016/0249912 A1 | 9/2016 | Fischvogt |
| 2016/0270835 A1 | 9/2016 | Reed |
| 2016/0278766 A1 | 9/2016 | Wenchell et al. |
| 2016/0338694 A1 | 11/2016 | Kayan |
| 2016/0345967 A1 | 12/2016 | Sniffin et al. |
| 2016/0354081 A1 * | 12/2016 | Ranucci ............. A61B 17/068 |
| 2017/0128068 A1 | 5/2017 | Zhang et al. |

(56) References Cited

U.S. PATENT DOCUMENTS

2017/0231631 A1 8/2017 Abuzaina et al.
2017/0265859 A1 9/2017 Sniffin et al.
2018/0042591 A1 2/2018 Russo et al.
2018/0116670 A1 5/2018 Fischvogt et al.

OTHER PUBLICATIONS

Extended European Search Report corresponding to EP 14 17 8107.0, completed Nov. 24, 2014 and dated Dec. 3, 2014; (5 pp).
Extended European Search Report corresponding to EP 14 17 4656.0, completed Jan. 16, 2015 and dated Jan. 26, 2015; (7 pp).
Extended European Search Report corresponding to EP 14 18 4907.5, completed Jan. 12, 2015 and dated Jan. 27, 2015; (9 pp).
European Search Report corresponding to EP 14 18 1900.3, completed Mar. 31, 2015 and dated Apr. 9, 2015; 7pp.
Extended European Search Report corresponding to EP 14 19 7885.8 dated Apr. 30, 2015.
Extended European Search Report corresponding to EP No. 11 25 0549.0, completed Sep. 9, 2013 and dated Sep. 17, 2013; 9 pages.
Extended European Search Report corresponding to EP 14 15 9394.7, completed Apr. 16, 2014 and dated Apr. 29, 2014; 8 pages.
European Search Report corresponding to EP 10 01 2659.8, completed Dec. 21, 2010; dated Jan. 3, 2011; 3 pages.
European Search Report corresponding to EP 10 01 2646.5, completed Feb. 11, 2011; dated Feb. 22, 2011.
Extended European Search Report corresponding to EP 14 15 1663.3 dated Jun. 7, 2016.
Supplementary European Search Report corresponding to EP 14 81 7036 dated Feb. 2, 2017.
European Search Report corresponding to EP 17 15 7259.7 dated May 10, 2017.
Chinese First Office Action corresponding to CN 201480037169.2 dated Jun. 29, 2017.
Chinese First Office Action corresponding to CN 201410418879.1 dated Jun. 29, 2017.
European Office Action corresponding to EP 14 17 8107.0 dated Oct. 12, 2017.
Australian Examination Report No. 1 corresponding to AU 2014200870 dated Oct. 26, 2017.
Chinese Second Office Action corresponding to CN 201410090675 dated Nov. 6, 2017.
Japanese Office Action corresponding to JP 2014-048652 dated Nov. 14, 2017.
Japanese Office Action corresponding to JP 2014-047708 dated Nov. 14, 2017.
Chinese Second Office Action corresponding to CN 2014103063407 dated Feb. 1, 2018.
Australian Examination Report No. 1 corresponding to AU 2014202970 dated Mar. 9, 2018.
Japanese Office Action corresponding to JP 2014-048652 dated Mar. 15, 2018.
Chinese Second Office Action corresponding to CN 201480077682.4 dated Mar. 21, 2018.
Australian Examination Report No. 1 corresponding to AU 2014202972 dated Mar. 27, 2018.
European Office Action corresponding to Patent Application EP 14 15 8946.5 dated Apr. 26, 2018.
Japanese Office Action corresponding to Patent Application JP 2014-132105 dated May 1, 2018.
Japanese Office Action corresponding to Patent Application JP 2014-047708 dated May 14, 2018.
Chinese Second Office Action corresponding to Patent Application CN 2014103559671 dated May 25, 2018.
Australian Examination Report No. 1 corresponding to Patent Application AU 2014302551 dated Jul. 16, 2018.
Japanese Office Action corresponding to Patent Application JP 2014-047708 dated Aug. 15, 2018.
Extended European Search Report dated Sep. 10, 2019 corresponding to counterpart Patent Application EP 19183028.0.

* cited by examiner

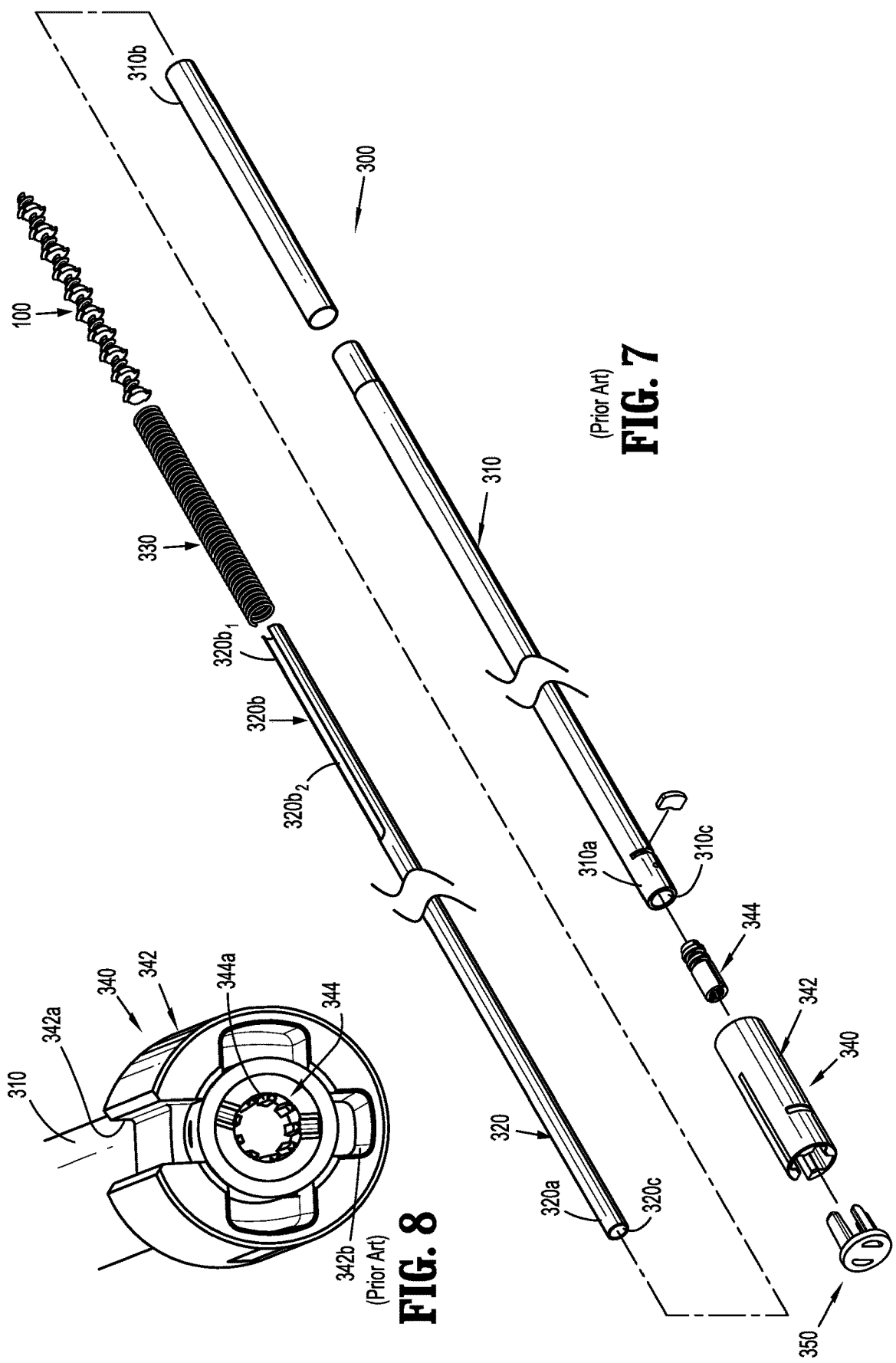

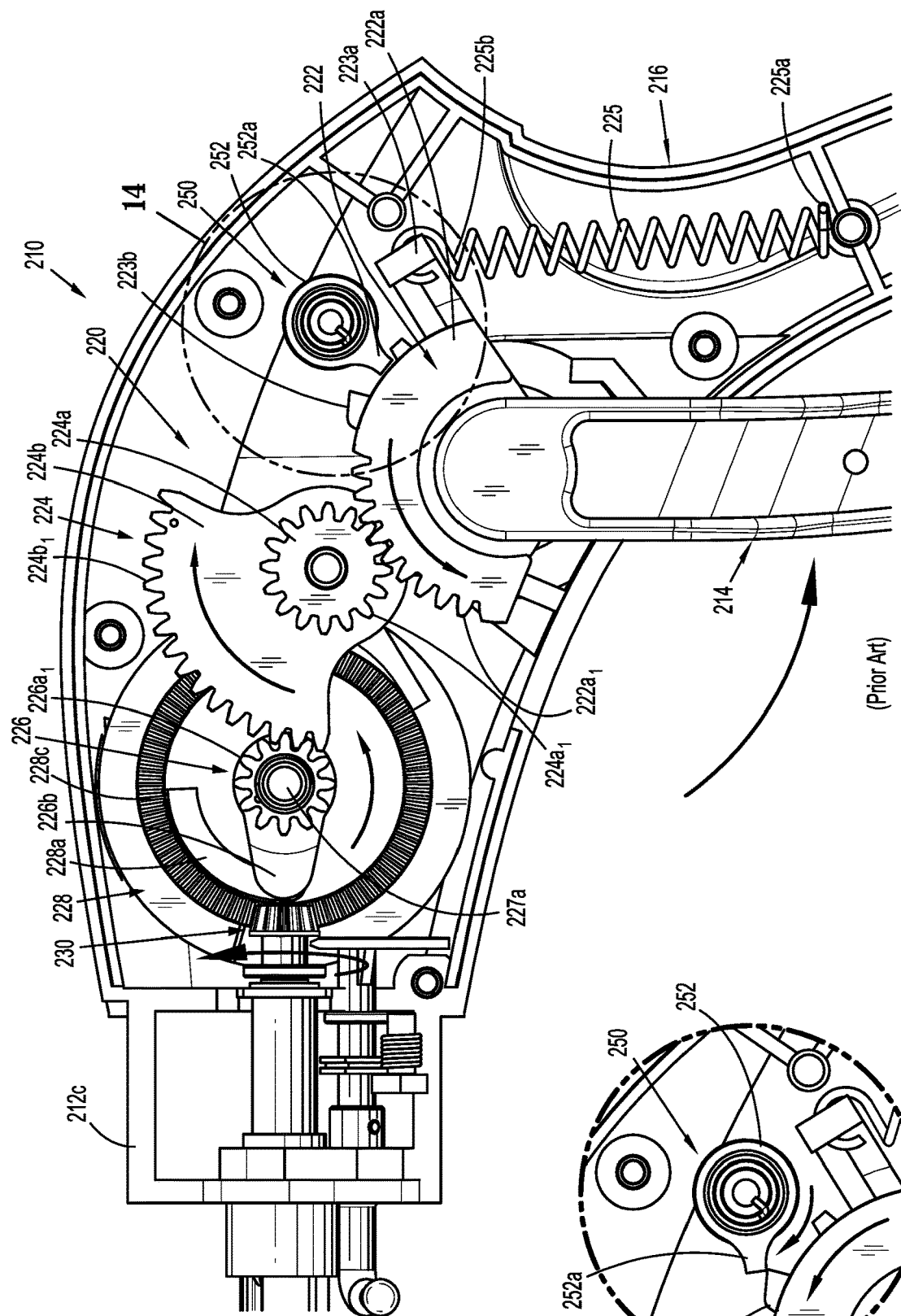
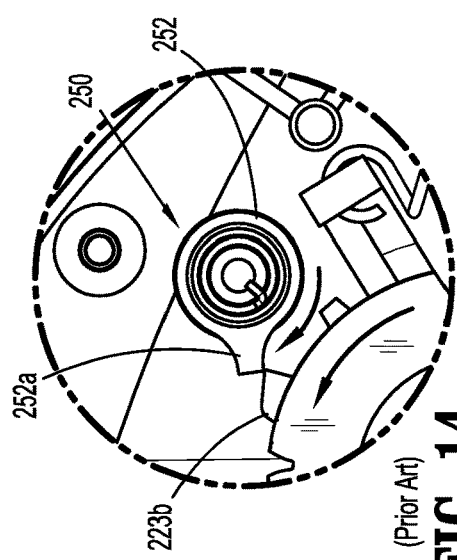
FIG. 13 (Prior Art)
FIG. 14 (Prior Art)

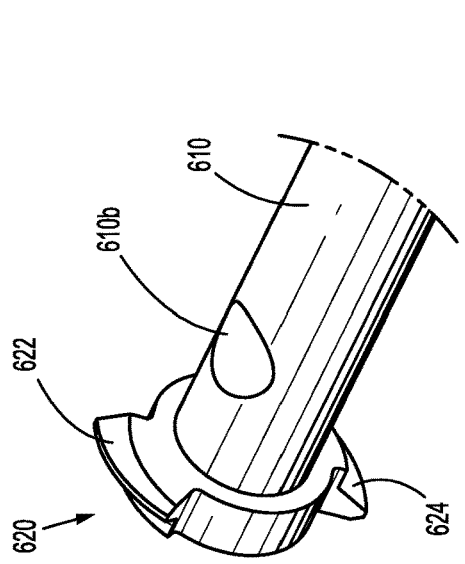
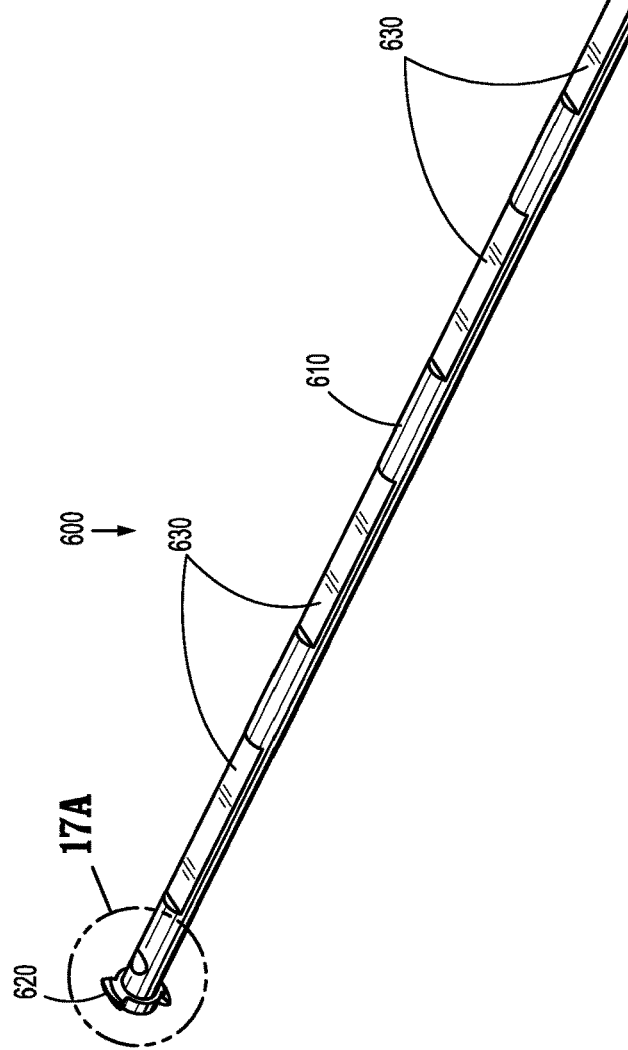
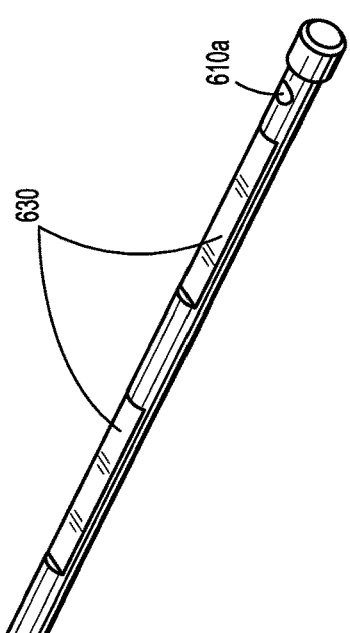
FIG. 17A
FIG. 17

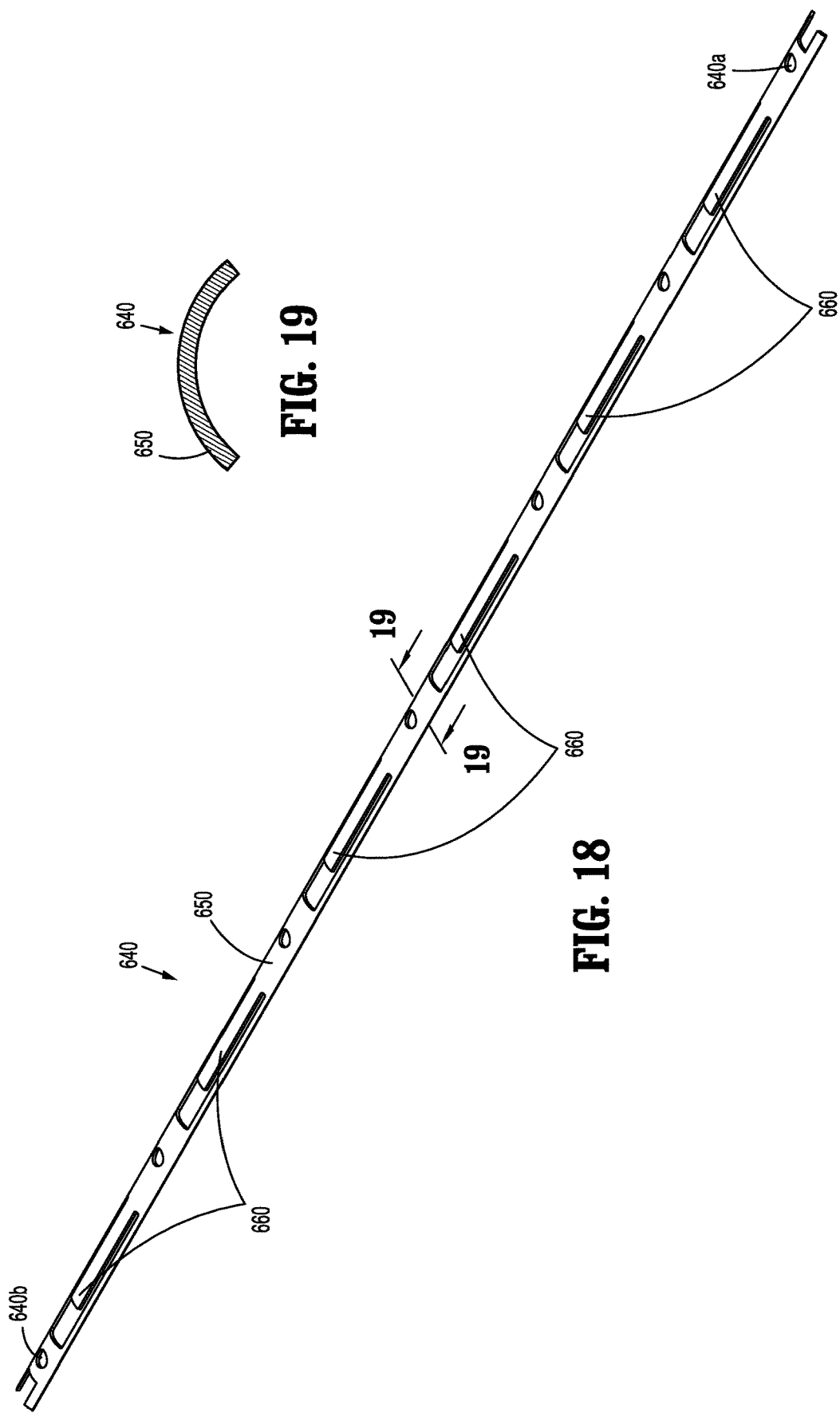
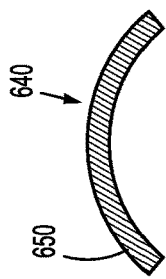
FIG. 18
FIG. 19

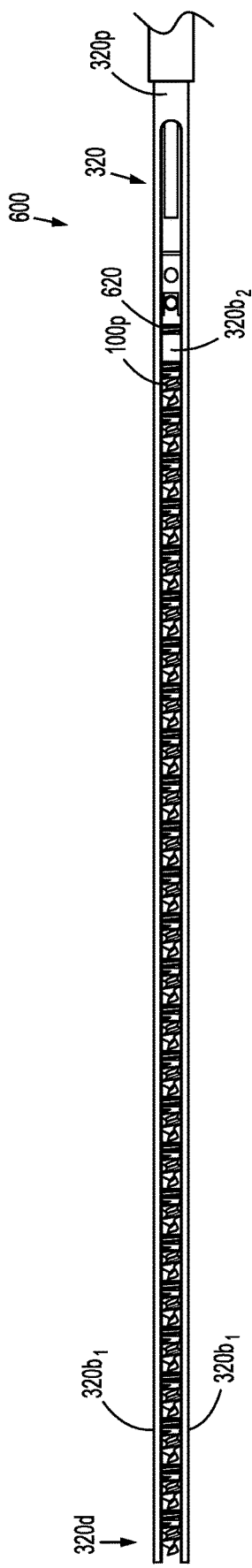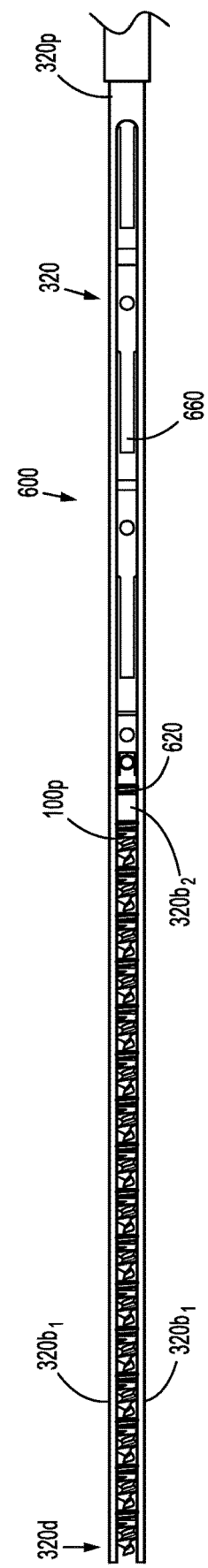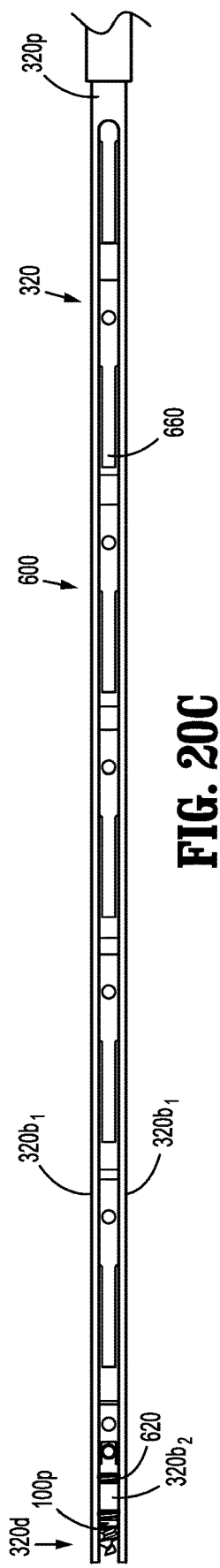

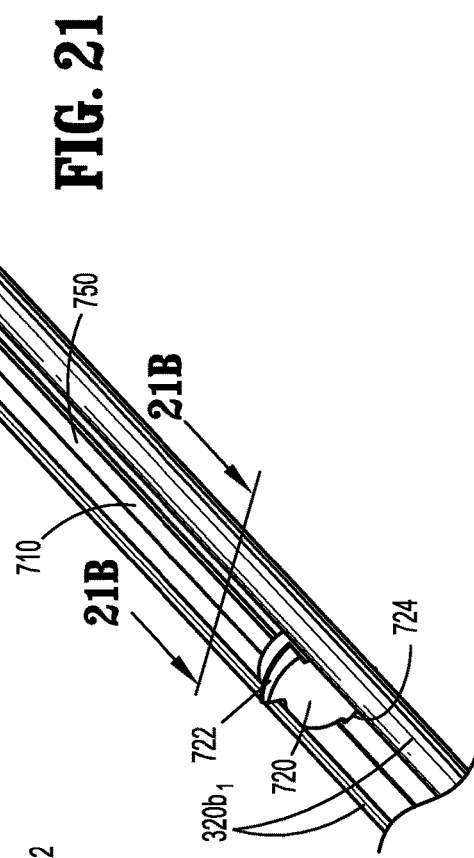
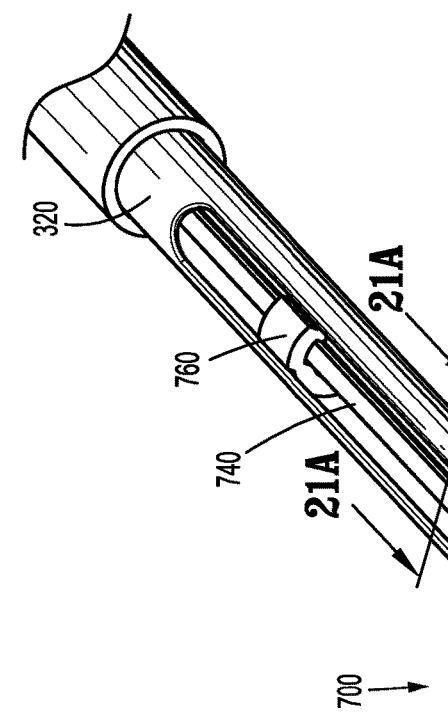
FIG. 21
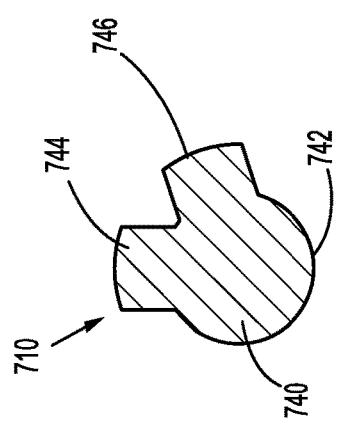
FIG. 21A
FIG. 21B

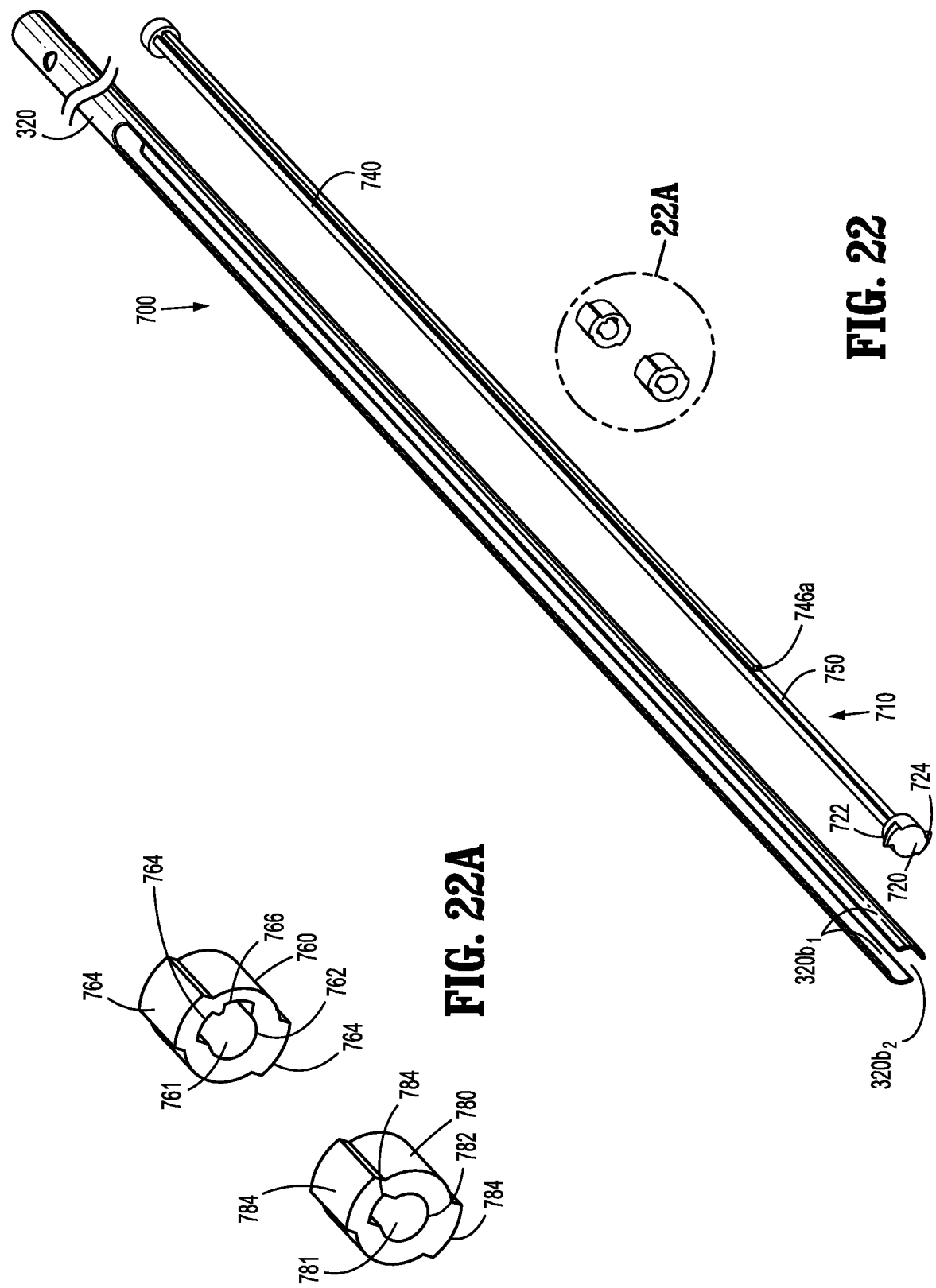

SURGICAL FASTENER APPLYING DEVICE, KITS AND METHODS FOR ENDOSCOPIC PROCEDURES

CROSS-REFERENCE TO RELATED APPLICATION

This application claims the benefit of and priority to U.S. Provisional Patent Application No. 62/691,137 filed Jun. 28, 2018, the entire disclosure of which is incorporated by reference herein.

BACKGROUND

1. Technical Field

The present disclosure relates to a surgical apparatus, device and/or system for performing endoscopic surgical procedures and methods of use thereof. More specifically, the present disclosure relates to a surgical fastener applying apparatus, device and/or system for performing endoscopic surgical procedures, which is loadable with disposable endoscopic loading units containing absorbable or permanent surgical fasteners, to kits, and methods of use thereof.

2. Background of Related Art

Various surgical procedures require instruments capable of applying fasteners to tissue to form tissue connections or to secure objects to tissue. For example, during hernia repair it is often desirable to fasten a mesh to body tissue. In certain hernias, such as direct or indirect inguinal hernias, a part of the intestine protrudes through a defect in the abdominal wall to form a hernial sac. The defect may be repaired using an open surgery procedure in which a relatively large incision is made and the hernia is closed outside the abdominal wall by suturing. The mesh is attached with sutures over the opening in the abdominal wall to provide reinforcement.

Minimally invasive, e.g., endoscopic or laparoscopic, surgical procedures are currently available to repair a hernia. In laparoscopic procedures, surgery is performed in the abdomen through a small incision while in endoscopic procedures, surgery is performed through narrow endoscopic tubes or cannulas inserted through small incisions in the body. Laparoscopic and endoscopic procedures generally utilize long and narrow instruments capable of reaching remote regions within the body and configured to seal with the incision or tube they are inserted through. Additionally, the instruments must be capable of being actuated remotely, that is, from outside the body.

Currently, minimally invasive surgical techniques for hernia repair utilize surgical fasteners, e.g., surgical tacks, staples, and clips, to secure the mesh to the tissue to provide reinforcement and structure for encouraging tissue ingrowth. Surgical fasteners are often applied through an elongate instrument for delivery to the mesh, and are manipulated from outside a body cavity.

In some procedures permanent fasteners may be required, while in other procedures bioabsorbable fasteners may be required, or both. The laparoscopic or endoscopic instruments are typically loaded with either permanent fasteners or bioabsorbable fasteners. Additionally, following a surgical procedure, these laparoscopic or endoscopic instruments are typically disposed.

Accordingly, a need exists for endoscopic or laparoscopic surgical devices which can be loaded with either permanent fasteners or bioabsorbable fasteners as needed or desired, and which may be at least partially re-used for continuing the surgical procedure and/or for a following surgical procedure.

SUMMARY

The present disclosure relates to surgical devices for performing endoscopic surgical procedures which are loadable with disposable endoscopic loading units loaded with absorbable or permanent surgical fasteners, kits, and methods of use thereof.

According to an aspect of the present disclosure, a surgical device is provided and includes a handle housing, an endoscopic assembly, and a follower assembly. The endoscopic assembly extends distally from the handle housing and includes an inner tube defining a longitudinal axis. The inner tube includes a distal portion defining a pair of opposed tines. The endoscopic assembly is configured to support a plurality of anchors at least partially therein. The follower assembly is disposed at least partially within the inner tube at a location proximal of the plurality of anchors, and includes a head and a shaft. A portion of the head is disposed between the pair of opposed tines. Actuation of the endoscopic surgical device causes rotation of the inner tube about the longitudinal axis relative to the handle housing, and causes distal advancement of the follower assembly relative to the inner tube.

In disclosed embodiments, the head of the follower assembly is disposed at a distal end of the shaft.

It is disclosed that the follower assembly includes a first ring disposed on the shaft, and that the first ring is longitudinally movable relative to the shaft. In embodiments, a proximal portion of the shaft of the follower assembly includes a first profile, a distal portion of the shaft of the follower assembly includes a second profile, and the first profile is different from the second profile.

It is further disclosed that the first ring is positionable on the distal portion of the shaft and is physically prevented from being positioned on the proximal portion of the shaft. In embodiments, after a predetermined amount of longitudinal movement of the shaft of the follower assembly relative to the inner tube, the proximal portion of the shaft forces the first ring distally relative to the inner tube. It is also disclosed that the follower assembly includes a second ring disposed on the shaft, and that the second ring is longitudinally movable relative to the shaft. In embodiments, the second ring is positionable on the distal portion of the shaft and on the proximal portion of the shaft.

In disclosed embodiments, the first ring defines a first aperture, the second ring defines a second aperture, and the first aperture has a different profile than the second aperture.

It is also disclosed that the follower assembly includes a plate having a plurality of fingers, and that the plate disposed in operative engagement with the shaft. In embodiments, each finger of the plurality of fingers of the plate of the follower assembly is biased away from the shaft. Further, the follower assembly is movable between a first position where at least one finger of the plurality of fingers is positioned proximally of the pair of opposed tines and a second position where the at least one finger of the plurality of fingers is positioned distally of the pair of opposed tines. Additionally, it is disclosed that when the follower assembly is in the second position, part of the at least one finger that is positioned distally of the pair of opposed tines is positioned between the pair of opposed tines.

In disclosed embodiments, the surgical device includes a coil disposed within the inner tube. The head of the follower assembly is disposed in operative engagement with the coil, and the follower assembly is longitudinally movable relative to the coil.

It is further disclosed that the surgical device includes a plurality of anchors disposed at least partially within the endoscopic assembly and disposed distally of the head of the follower assembly.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 7 is a perspective view, with parts separated, of the endoscopic assembly of the surgical device of the present disclosure;

FIG. 8 is a rear, perspective view of the endoscopic assembly of the present disclosure;

FIG. 13 is a side elevational view of the handle assembly, with a housing half-section removed therefrom, illustrating the handle assembly during a firing stroke of the endoscopic surgical device;

FIG. 14 is an enlarged view of the indicated area of detail of FIG. 13;

FIG. 17 is a perspective view of a portion of a follower assembly according to another aspect of the present disclosure;

FIG. 17A is an enlarged view of the area of detail depicted in FIG. 17;

FIG. 18 is a perspective view of another portion of the follower assembly of FIG. 17;

FIG. 19 is a cross-sectional view as taken through section line 19-19 of FIG. 18;

FIGS. 20A-20C are tops views of the follower assembly of FIGS. 17-19 in various stages of use engaged with an endoscopic surgical device of the present disclosure;

FIG. 21 is a perspective view of a portion of another follower assembly engaged with an endoscopic surgical device of the present disclosure;

FIG. 21A is a cross-sectional view as taken through section line 21A-21A of FIG. 21;

FIG. 21B is a cross-sectional view as taken through section line 21B-21B of FIG. 21;

FIG. 22 is a perspective, assembly view of the follower assembly of FIG. 21; and FIG. 22A is an enlarged view of the area of detail depicted in FIG. 22.

DETAILED DESCRIPTION OF EMBODIMENTS

Figure 1:
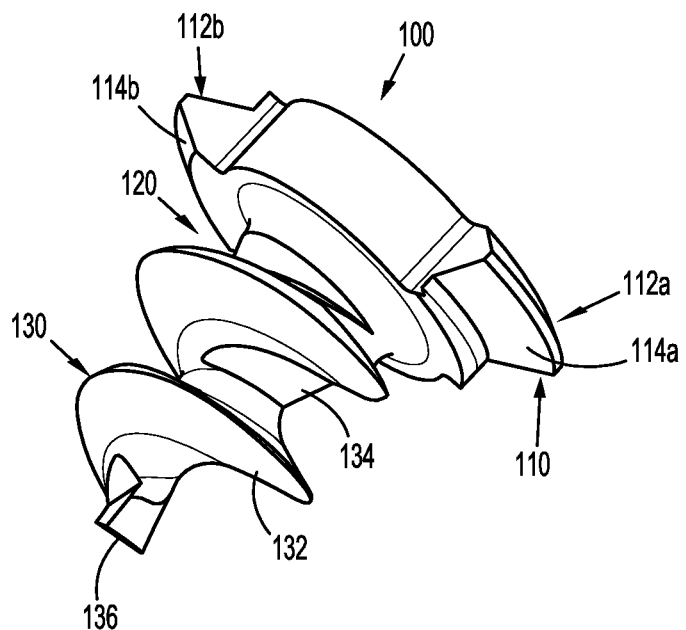
FIG. 1 is a perspective view of a surgical anchor for use in an endoscopic surgical device in accordance with the present disclosure.
Figure 2:
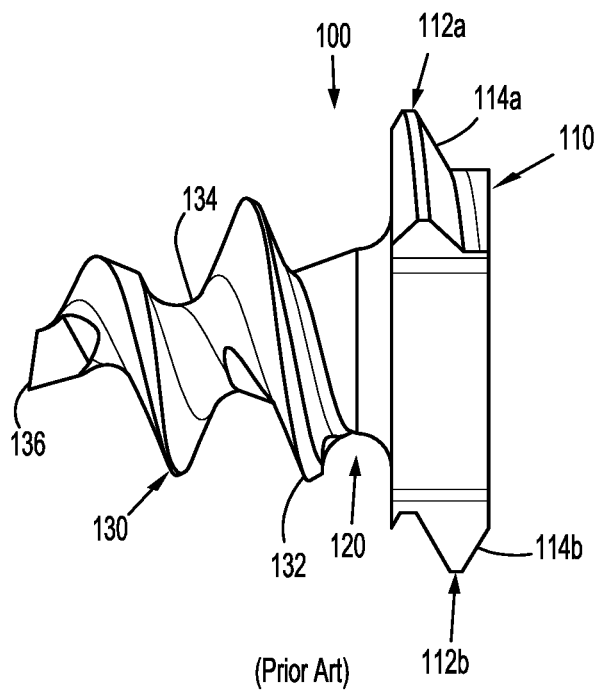
FIG. 2 is a side, elevational view of the surgical anchor of FIG. 1.
Figure 3:
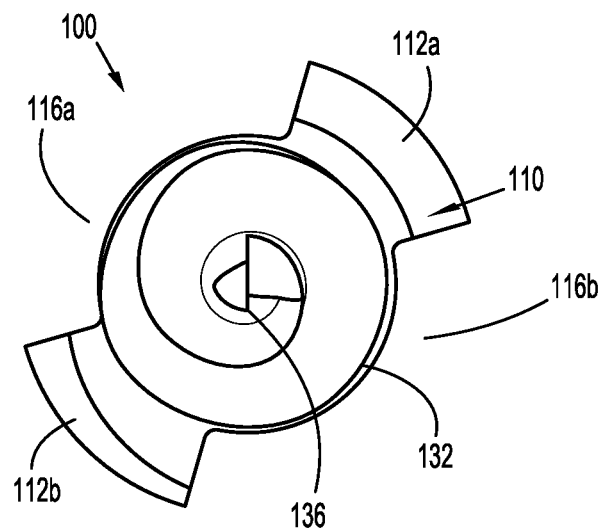
FIG. 3 is a distal, end view of the surgical anchor of FIGS. 1 and 2.

Embodiments of the presently disclosed endoscopic surgical device is described in detail with reference to the drawings, in which like reference numerals designate identical or corresponding elements in each of the several views. As used herein the term "distal" refers to that portion of the endoscopic surgical device, that is farther from the user, while the term "proximal" refers to that portion of the endoscopic surgical device that is closer to the user.

Referring initially to FIGS. 1-4, a surgical anchor for use with the surgical tack applier of the present disclosure is illustrated and generally designated as anchor 100. As illustrated in FIGS. 1-4, anchor 100 includes a head section 110, a mesh retention section 120, and a threaded tissue-snaring section 130. Head section 110 includes a pair of opposing threaded sections 112a, 112b having respective radially, outer, helical head threads 114a, 114b, and a pair of opposing open or slotted sections 116a, 116b. A distal surface of head section 110 is formed onto or integral with a proximal end of mesh retention section 120.

Mesh retention section 120 of anchor 100 extends from and between a distal end or surface of head section 110 and a proximal end of tissue-snaring section 130. Mesh retention section 120 functions to lock, anchor or otherwise retain a surgical mesh (not shown) on to anchor 100 when anchor 100 is screwed into the mesh to a depth past a proximal-most segment 138 of tissue-snaring thread 132 of tissue-snaring section 130. This is achieved because there is no thread located in mesh retention section 120 that would allow anchor 100 to be unscrewed or backed out from the mesh.

Mesh retention section 120 has a cylindrical or conical transverse cross-sectional profile. Mesh retention section 120 includes a transverse radial dimension, relative to a central longitudinal axis of anchor 100, that is smaller than a transverse radial dimension of head section 110, and smaller than a transverse radial dimension of proximal-most segment 138 of tissue-snaring thread 132.

Threaded tissue-snaring section 130 of anchor 100 includes helical threads 132 formed onto a tapered truncated body section 134. A distal point or tip 136 defines the terminus of the distal most tissue-snaring thread 132.

Figure 4:
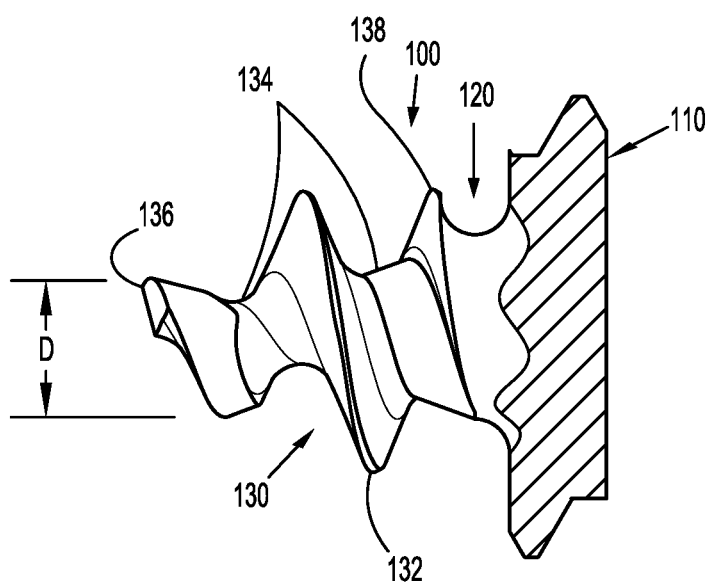
FIG. 4 is a side, elevational view, partially broken away, of the surgical anchor of FIGS. 1-3.
Figure 5:
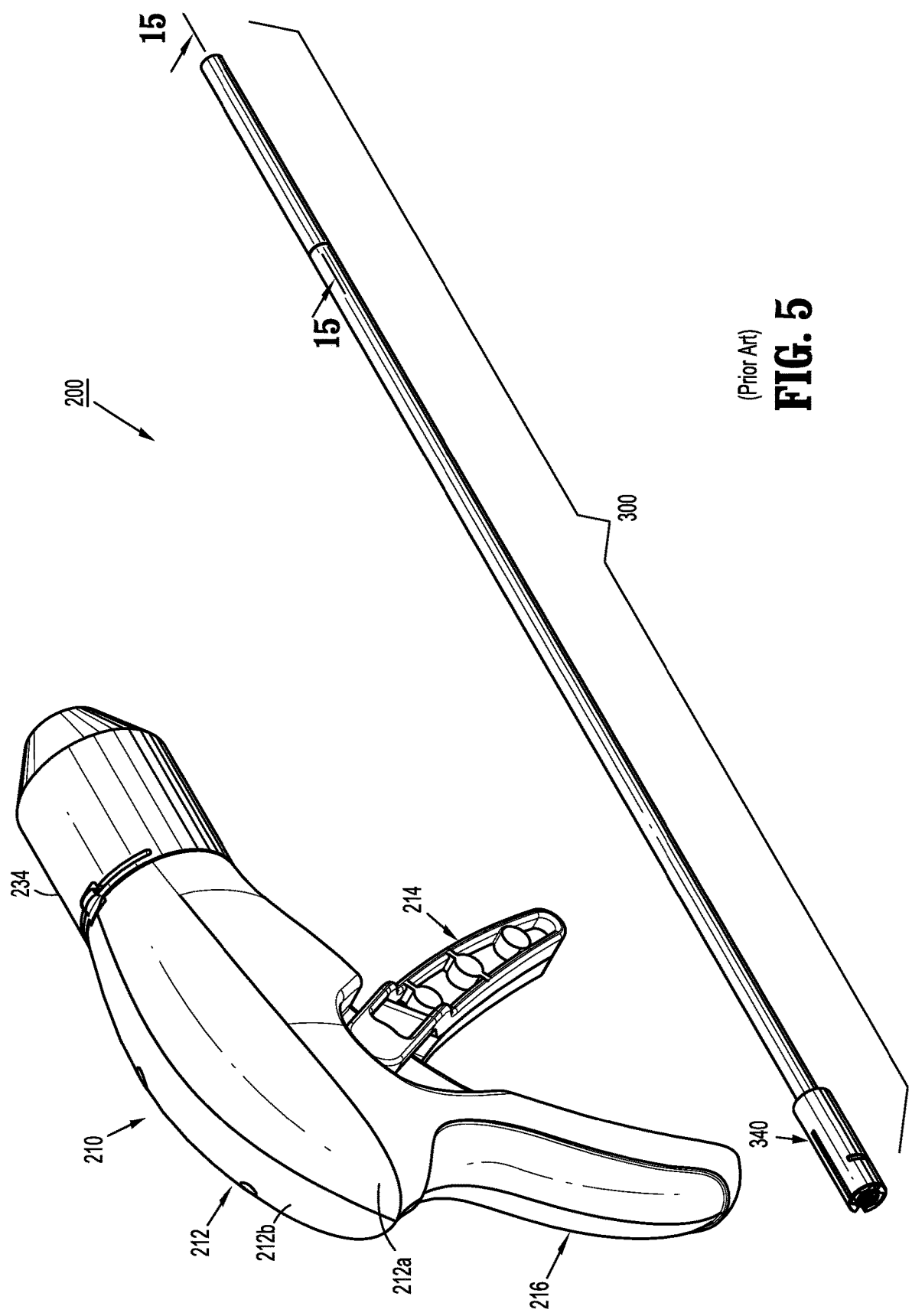
FIG. 5 is a rear, perspective view of an endoscopic surgical device according to an aspect of the present disclosure, illustrating a handle assembly and an endoscopic assembly thereof separated from one another.

As shown in FIG. 4, body section 134 of tissue-snaring section 130 is tapered, e.g., becoming smaller toward the distal end of threaded tissue-snaring section 130, and terminates or truncates to a distal truncation point "TP", prior to reaching an apex or tip of anchor 100. Body section 134 includes a concave taper such that, for a given length, a minimum diameter body section 134 is defined upon truncation thereof which is approximately less than 0.01 inches.

Anchor 100 includes a transverse dimension "D", of a distal-most thread in the threaded tissue-snaring section 130 which is as large as design constraints will allow or approximately greater than 0.040 inches. In accordance with the present disclosure, a small truncated body diameter and a large value of "D" minimizes tissue indentation. The tissue-snaring threads 132 terminate at distal tip 136, which is distal of the truncation point "TP" of body section 134.

By providing a distal tip 136 extending distally of truncation point "TP" of tissue-snaring section 130, a penetration of the mesh, by anchor 100, is eased; and an indentation of the mesh into relatively soft tissue, by anchor 100, is minimized, as compared to an anchor having a non-truncated body with tapered threads.

For a given force applied to a surgical mesh by the surgeon, exerting a distal force on a tack applier, the larger the dimension "D" of anchor 100, the less the distal force that needs to be exerted in order to cause indentation of an underlying tissue and surgical mesh.

Anchor 100 is non-cannulated and is constructed from a suitable bioabsorbable material, such as, for example, polylactide, polyglycolide. Anchor 100 is formed from a proprietary biocompatible co-polymer (Lactomer USS L1, Boehringer Ingelheim LR 704 S, or Boehringer Ingelheim LG-857). Anchor may also be constructed from suitable non-bioabsorbable materials, or permanent material, such as, for example, stainless steel, titanium and the like.

Figure 15:
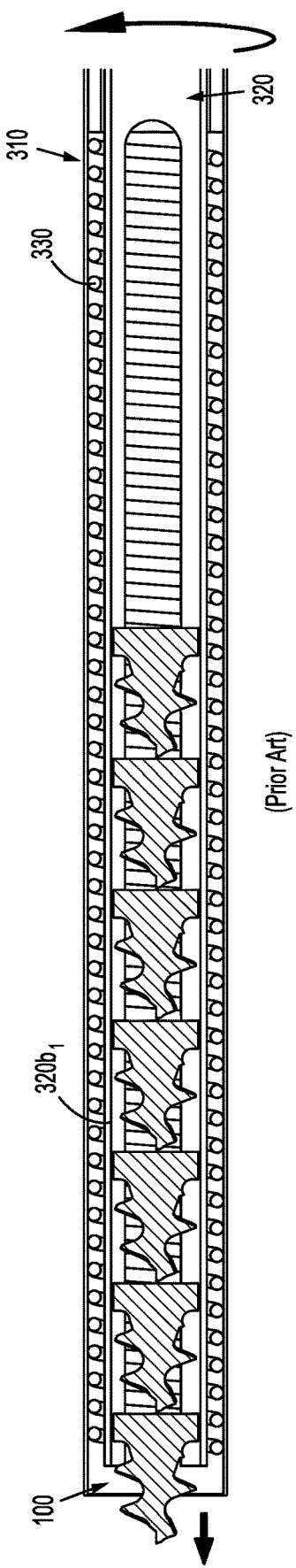
FIG. 15 is a cross-sectional view of the distal end portion of the endoscopic assembly, as taken through section line 15-15 of FIG. 5, illustrating the endoscopic assembly during a firing stroke of the endoscopic surgical device.
Figure 16:
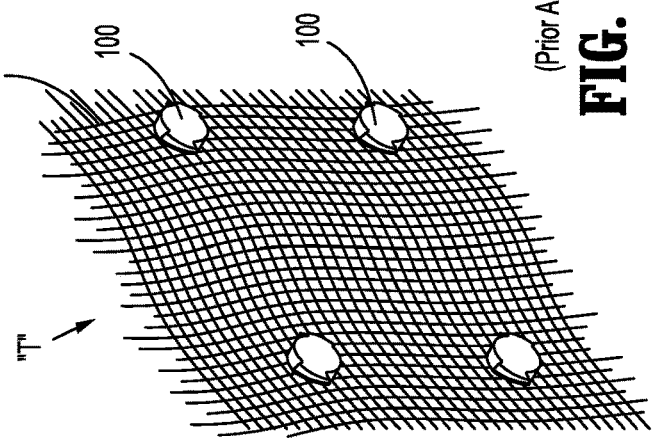
FIG. 16 is an illustration of surgical anchors of the present disclosure fixing a surgical mesh in place.

Turning now to FIGS. 5-16, an endoscopic surgical device, in the form of an endoscopic surgical tack applier or tacker, is shown generally as 200. Tack applier 200 includes a handle assembly 210, and a removable endoscopic assembly 300 (e.g., single use loading unit SULU) extending from handle assembly 210 and configured to store and selectively release or fire a plurality of anchors 100 therefrom and into mesh "M" overlying tissue "T". (FIG. 16).

Handle assembly 210 includes a handle housing 212 formed from a first half-section 212a and a second half section 212b joined to one another. First half-section 212a and second half section 212b of handle housing 212 may be joined to one another using know methods by those of skill in the art, including and not limited to ultrasonic welding, fasteners (e.g., screws) and the like. First half-section 212a and second half section 212b of handle housing 212 are joined to one another such that a fluid-tight seal is provided therebetween.

Handle housing 212 defines a fixed handle portion 216 having a free end 216a. Handle assembly 210 includes a trigger 214 pivotably connected to handle housing 212, at a pivot point disposed within handle housing 212. Trigger 214 includes a free end 214a spaced a distance from fixed handle portion 216 when trigger 214 is in an extended or un-actuated condition. Trigger 214 includes a pivot end 214b extending therefrom and extending into handle housing 212 through a side of handle housing 212.

A fluid-tight seal may be provided between pivot end 214b of trigger 214 and handle housing 212. In accordance with the present disclosure, an X-ring or the like, including an o-ring, etc., (not shown) may be used between pivot end 214b of trigger 214 and handle housing 212.

Figure 6:
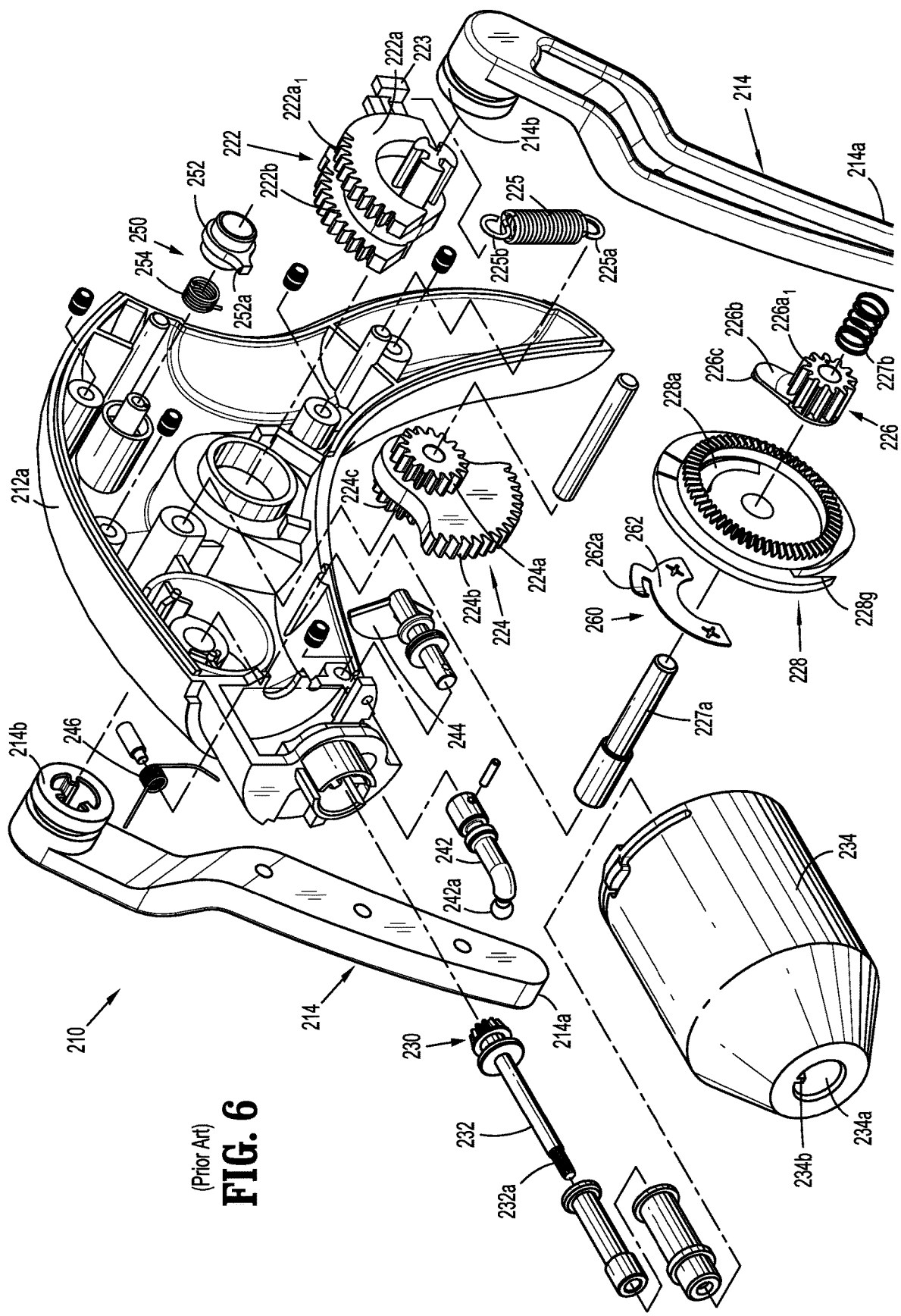
FIG. 6 is a left, front, perspective view, with parts separated, of the surgical device of FIG. 5, illustrating a half-section of the handle assembly removed therefrom.

As illustrated in FIG. 6, handle assembly 210 supports a gear train 220 within handle housing 212. Gear train 220 includes a trigger or drive gear 222 keyed to or non-rotatably connected to pivot end 214b of trigger 214. Drive gear 222 is a two tiered gear including a first drive gear 222a, and a second drive gear 222b. First drive gear 222a may be in the form of a quadrant gear or the like having a plurality of gear teeth $222a_1$ formed along a radial outer edge thereof and extending along an arcuate length of first drive gear 222a. First drive gear 222a includes a stem or stopper 223a extending radially therefrom, at a location proximal of gear teeth $222a_1$. Second drive gear 222b defines a plurality of gear teeth $222b_1$ formed along a radial outer edge thereof.

Gear train 220 further includes a transmission gear assembly 224 pivotably supported in handle housing 212. Transmission gear assembly 224 is a three tiered gear including a first transmission gear 224a, a second transmission gear 224b, and third transmission gear 224c each rotatably supported on a common pivot axis. First transmission gear 224a may be in the form of a pinion gear or the like having a plurality of gear teeth $224a_1$ formed along a radial outer edge thereof and being in meshing engagement with gear teeth $222a_1$ of first drive gear 222a. Second transmission gear 224b may be in the form of a quadrant gear or the like having a plurality of gear teeth $224b_1$ formed along a radial outer edge thereof and extending along an arcuate length of second transmission gear 224b. Third transmission gear 224c may be in the form of a pinion gear or the like having a plurality of gear teeth $224c_1$ formed along a radial outer edge thereof and being in meshing engagement with gear teeth $224b_1$ of second transmission gear 224b.

Gear train 220 also includes a clutch gear 226 pivotably and slidably supported on a pivot axis 227a in handle housing 212. Clutch gear 226 may be in the form of a pinion gear or the like having a plurality of gear teeth $226a_1$ formed along a radial outer edge thereof and being in meshing engagement with gear teeth $224b_1$ of second transmission gear 224b. Clutch gear 226 is biased into meshing engagement with second transmission gear 224b by a biasing member 227b (FIG. 6). Clutch gear 226 includes an arm 226b extending radially therefrom, and a cam or ramp 226c (FIG. 6) extending/projecting from arm 226b. Cam 226c includes a front end having a height defining a shoulder, and a tail end tapering into arm 226b.

Gear train 220 further includes a first bevel gear 228 pivotably and slidably supported on pivot axis 227a in handle housing 212. First bevel gear 228 may be in the form of a crown gear or the like. First bevel gear 228 is operatively engaged/associated with clutch gear 226. First bevel gear 228 defines an arcuate slot 228a formed in first face 228d thereof for selectively receiving and engaging cam 226c of clutch gear 226. Slot 228a includes a front end wall configured to engage the front end of cam 226c of clutch gear 226, and tapers along a length thereof to be flush with the first face of first bevel gear 228.

In operation, as trigger 214 of tacker 200 is actuated, trigger 214 causes drive gear 222 to be rotated, in a first direction. As drive gear 222 is rotated in the first direction, drive gear 222 causes first transmission gear 224a and second transmission gear 224b to be rotated, in a first direction, about the pivot axis thereof. As second transmission gear 224b is rotated in the first direction, second transmission gear 224b causes clutch gear 226 to be rotated, in a first direction, about a pivot axis thereof.

As clutch gear 226 is rotated in the first direction, the front end of cam 226c of clutch gear 226 is rotated in a first direction until the front end of cam 226c engages or contacts the front end wall of slot 228a of first bevel gear 228. After the front end of cam 226c of clutch gear 226 engages or contacts the front end wall of slot 228a of first bevel gear 228, continued rotation of clutch gear 226, in the first direction, results in concomitant rotation of first bevel gear 228 in a first direction. At this point, first bevel gear 228 continues to rotate in the first direction so long as trigger 214 is being actuated to a closed or fully actuated condition.

When actuation of trigger 214 is stopped, either prior to complete actuation or following complete actuation, rotation of first bevel gear 228, in the first direction, is also stopped. Upon the completion of a partial or complete actuation of trigger 214 and a release thereof, trigger 214 causes drive gear 222 to be rotated, in a second direction (opposite the first direction). As drive gear 222 is rotated in the second direction, drive gear 222 causes first transmission gear 224a and second transmission gear 224b to be rotated, in a second direction, about the pivot axis thereof. As second transmission gear 224b is rotated in the second direction, second transmission gear 224b causes clutch gear 226 to be rotated, in a second direction, about pivot axis 227a. As clutch gear 226 is rotated in the second direction, the tail end of cam 226c thereof slides along slot 228a of first bevel gear 228, and, if the rotation in the second direction is sufficient, slides out of slot 228a of first bevel gear 228 and along first face 228d of first bevel gear 228. As cam 226c of clutch gear 226 slides along slot 228a of first bevel gear 228, clutch gear 226 slides axially along pivot axis 227a and compresses biasing member 227b.

If trigger 214 was fully actuated, a complete release of trigger 214, will result in clutch gear 226 making a complete revolution, in the second direction, until the front end of cam 226c of clutch gear 226 clears the front end wall of slot 228b of first bevel gear 228 to thereby re-enter slot 228b of first bevel gear 228. Specifically, as the front end of cam 226c of clutch gear 226 clears the front end wall of slot 228b of first bevel gear 228, biasing member 227b forces clutch gear 226 axially along pivot axis 227a and cam 226c of clutch gear 226 back into slot 228b of first bevel gear 228.

Figure 12:
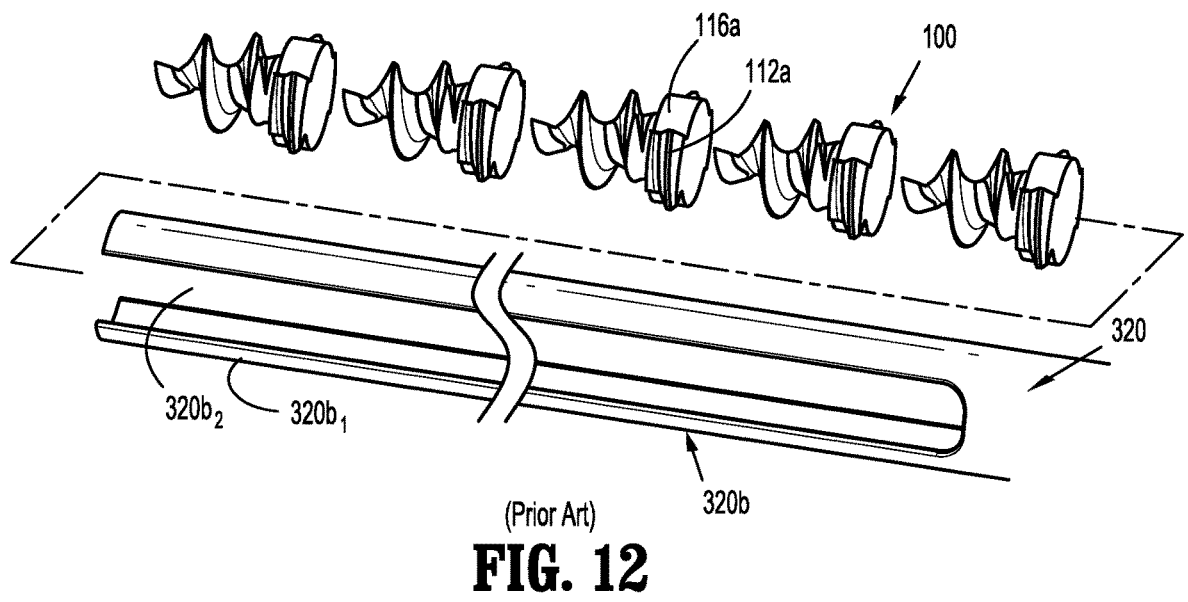
FIG. 12 is a perspective view of the distal end portion of the endoscopic assembly with the outer tube and the coil removed therefrom, shown with surgical anchors separated therefrom.

As illustrated in FIGS. 6 and 12, handle assembly 210 includes a biasing member 225 configured for maintaining trigger 214 in an extended or un-actuated position. Biasing member 225 is also configured to have a spring constant sufficient to return trigger 214 to the un-actuated position following a partial or complete actuation of trigger 214. Biasing member 225 includes a first end 225a fixedly connected in handle housing 212 and a second end 225b connected to stem 223a extending from first drive gear 222a.

With reference to FIGS. 6, 13 and 14, handle assembly 210 includes an audible/tactile feedback mechanism 250 supported within handle housing 212 and in operative association with drive gear 222. Specifically, audible/tactile feedback mechanism 250 includes a dial 252 rotatably supported in handle housing 212. Dial 252 includes a tooth 252a extending therefrom. Dial 252 is spring biased to a home position. Audible/tactile feedback mechanism 250 further includes a tooth or stem 223b extending from second drive gear 222b. In operation, as trigger 214 is actuated and second drive gear 222b rotated, stem 223b of second drive gear 222b contacts tooth 252a of dial 252 causing dial 252 to rotate against the bias of a spring member 254. When stem 223b of second drive gear 222b clears tooth 252a of dial 252, dial 252 is returned to or snapped back to the home position thereof due to the bias of spring member 254. When dial 252 is snapped back to the home position thereof, dial 252 creates an audible and/or tactile response.

As shown in FIG. 6, handle assembly 210 of tack applier 200 is provided with a ratchet mechanism 260 which is configured to inhibit or prevent inner tube 320 (FIGS. 7, 11 and 12) from backing-out or reversing after anchor 100 has been at least partially driven into tissue. Ratchet mechanism 260 includes, as seen in FIG. 6, a series of ratchet teeth 228f formed on a rear or second face of first bevel gear 228.

Ratchet mechanism 260 further includes a spring clip 262 secured within handle assembly 210. Spring clip 262 includes a resilient finger 262a configured for engagement with ratchet teeth 228f formed on rear surface of first bevel gear 228.

In operation, resilient finger 262a of spring clip 262 engages with ratchet teeth 228f of first bevel gear 228 in such a manner that as first bevel gear 228 is rotated, in a first direction, resilient finger 262a of spring clip 262 cams over ratchet teeth 228f and permits rotation of first bevel gear 228. Also, if first bevel gear 228 starts to rotate in a second direction (opposite to the first direction), resilient finger 262a of spring clip 262 stops along ratchet teeth 228f thereby preventing or inhibiting first bevel gear 228 from rotating in the second direction. As such, any reverse rotation or "backing-out" of anchor 100 or inner tube 320 of endoscopic assembly 300 (tending to cause first bevel gear 228 to rotate in the second direction), during a driving or firing stroke, is inhibited or prevented.

Figure 9:
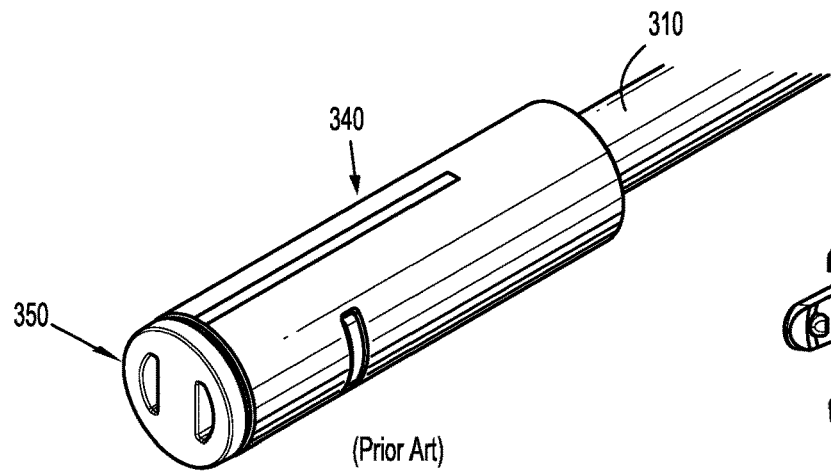
FIG. 9 is a rear, perspective view of the endoscopic assembly of the present disclosure, illustrating a shipping plug connected thereto.
Figure 10:
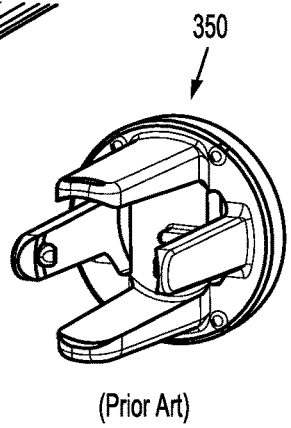
FIG. 10 is a perspective view of the shipping plug of the present disclosure.
Figure 11:
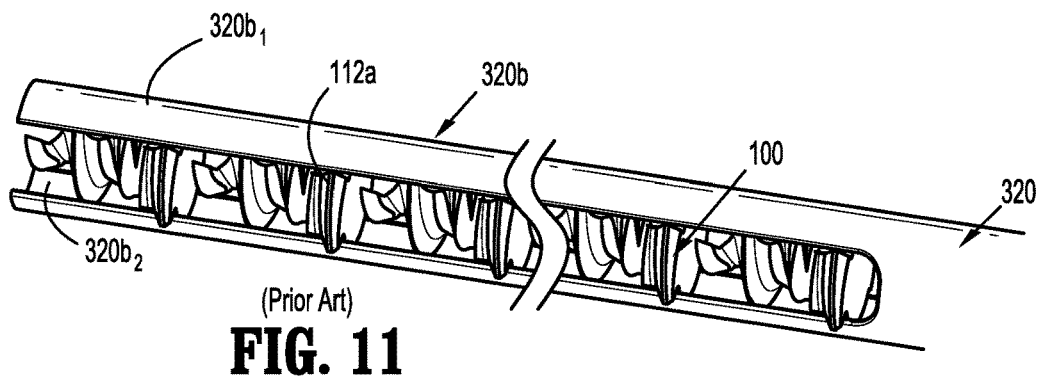
FIG. 11 is a perspective view of a distal end portion of the endoscopic assembly with an outer tube and a coil removed therefrom, shown with surgical anchors loaded therein.

With reference to FIGS. 6 and 13, handle assembly 210 further includes a second or pinion-bevel gear 230 rotatably supported in a distal end of handle housing 212. Pinion-bevel gear 230 includes gear teeth 230a operatively engaged or meshed with gear teeth 228c formed on the front face of first bevel gear 228. Pinion-bevel gear 230 is non-rotatably secured to a drive shaft 232 extending distally from handle housing 212. Drive shaft 232 is configured and dimensioned to engage an inner connector member 344 of endoscopic assembly 300 (FIGS. 8 and 9). In an embodiment, drive shaft 232 defines a plurality of axially extending ribs 232a at a distal end thereof.

In operation, upon squeezing of trigger 214, gear train 220 causes pinion-bevel gear 230 to rotate in a first direction. As pinion-bevel gear 230 is rotated in the first direction, pinion-bevel gear 230 transmits the rotation to inner tube 320 of endoscopic assembly 300.

Handle assembly 210 includes a ferrule or collar 234 rotatably and removably supported on handle housing 212. Ferrule 234 defines a distal opening 234a that is axially aligned with drive shaft 232. Ferrule 234 includes a stopper or tooth 234b extending radially into distal opening 234a.

Ferrule 234 is rotatable between a lock position (anchor retaining/advancing assembly 300 is locked to handle assembly 212, and tacker 200 is ready to fire,); an exchange position (anchor retaining/advancing assembly 300 can be connected/disconnected to/from handle assembly 212, and tacker 200 cannot be fired); and a ferrule release position (ferrule 234 can be removed from handle housing 212, and handle housing 212 may be cleaned or sterilized).

Turning now to FIGS. 5-12, as illustrated therein, endoscopic assembly 300 includes an outer tube 310, an inner tube 320 rotatably disposed within outer tube 310, a guide coil or spring 330 disposed between outer tube 310 and inner tube 320, a plurality of anchors 100 loaded within inner tube 310, and a connector 340 supported at a proximal end of outer tube 310 and inner tube 320.

Outer tube 310 of endoscopic assembly 300 includes a proximal end 310a and a distal end 310b, and defines a lumen 310c therethrough. As described briefly above, endoscopic assembly 300 further includes a guide coil or spring 330 fixedly disposed within at least a distal portion of outer tube 310.

Endoscopic assembly 300 also includes an inner tube 320 rotatably disposed within coil 330. Inner tube 320 includes a proximal end portion 320a and a splined distal end portion 320b, and defines a lumen 320c therethrough.

Distal end portion 320b of inner tube 320 is slotted, defining a pair of opposed tines $320b_1$ and a pair of opposed channels $320b_2$. Distal end portion 320b of inner tube 320 is capable of accepting a plurality of anchors 100 within inner tube 320. In particular, anchors 100 are loaded into endoscopic assembly 300 such that the pair of opposing threaded sections 112a, 112b of anchors 100 extend through respective channels $320b_2$ of distal end portion 320b of inner tube 320 and are slidably disposed within the groove of coil 330, and the pair of tines $320b_1$ of distal end portion 320b of inner tube 320 are disposed within the pair of slotted sections 116a, 116b of anchors 100.

In use, as inner tube 320 is rotated, about its longitudinal axis, with respect to coil 330, the pair of tines $320b_1$ of inner tube 320 transmit the rotation to anchors 100 and advance anchors 100 distally owing to head threads 114a, 114b of anchors 100 engaging with coil 330.

As illustrated specifically in FIGS. 7 and 8, endoscopic assembly 300 includes a connector 340 having an outer connector member 342 non-rotatably connected to proximal end 310a of outer tube 310, and an inner connector member 344 non-rotatably connected to proximal end 320a of inner tube 320. Inner connector member 344 is nested within outer connector member 342. Outer connector member 342 is substantially cylindrical and defines at least one longitudinally extending outer radial groove 342a that extends through a proximal end thereof, and at least one longitudinally extending inner groove 342b. Outer connector member 342 is sized and shaped to be inserted into distal opening 234a of ferrule 234 of handle assembly 210 and into annular wall 212h of nose 212c of handle housing 212.

Inner connector member 344 is substantially cylindrical and defines at least one longitudinally extending inner rib 344a projecting radially into a lumen thereof.

In order to connect endoscopic assembly 300 to handle assembly 210, with ferrule 234 in the exchange position, outer radial groove 342a of outer connector member 342 is first aligned with stopper or tooth 234b of ferrule 234 and with tooth 212i of annular wall 212h of nose 212c. Then, outer connector member 342 is fully inserted into ferrule 234 and annular wall 212h, tooth 212i of annular wall 212h of nose 212c is disposed within outer radial groove 342a of outer connector member 342, and stopper or tooth 234b of ferrule 234 is disposed distally of outer connector member 342.

When outer connector member 342 is fully inserted into ferrule 234 and annular wall 212h, the distal end of drive shaft 232 enters into inner connector member 344 such that the at least one longitudinally extending inner rib 344a of inner connector member 344 mechanically engages or meshes with the plurality of axially extending ribs 232a provided at the distal end of drive shaft 232.

With outer connector member 342 is fully inserted into ferrule 234 and annular wall 212h, ferrule 234 is rotated from the exchange position to the lock position, whereby stopper or tooth 234b of ferrule 234 is rotated to a radial position, out of alignment with outer radial groove 342a of outer connector member 342, to block withdrawal of outer connector member 342 from within ferrule 234 and from within annular wall 212h of nose 212c of handle housing 212.

As illustrated in FIGS. 7-10, endoscopic assembly 300 includes a shipping wedge, plug or cap 350 configured and adapted for selective connection to connector 340. Cap 350 includes an end wall 352, at least one leg 354 extending from end wall 352 and being configured and dimensioned for selective receipt in a respective longitudinally extending outer radial groove 342a (FIG. 8) of outer connector member 342, and a stem (not shown) extending from end wall 352 and being configured and dimensioned for selective receipt into inner connector member 344 for engagement with longitudinally extending inner rib(s) 344a of inner connector member 344. When cap 350 is secured to connector 340, the at least one leg 354 and the stem of cap 350 engage outer connector member 342 and inner connector member 344 to prevent their rotation relative to one another.

Cap 350 is used to fix the radial position of inner tube 320 relative to outer tube 310 and thus ensure that the stack of surgical anchors 100 are not prematurely advanced through endoscopic assembly 300 prior to connection of endoscopic assembly 300 to handle assembly 210. If the stack of surgical anchors 100 are advanced through endoscopic assembly 300, prior to connection of endoscopic assembly 300 to handle assembly 210, a timing of the firing of tack applier 200 may be effected, whereby each fully stroke of trigger 214 may either not fully fire a surgical anchor 100 from endoscopic assembly 300 or may begin to fire a second surgical anchor 100 from endoscopic assembly 300.

In an operation of surgical tacker 200, as illustrated in FIGS. 13-15, with endoscopic assembly 300 operatively connected and locked to handle assembly 210, as described above, as drive shaft 232 is rotated due to an actuation of trigger 214, also as described above, said rotation is transmitted to inner tube 320 of endoscopic assembly 300 via the engagement of the plurality of axially extending ribs 232a provided at the distal end of drive shaft 232 with the at least one longitudinally extending inner rib 344a of inner connector member 344.

Again, as inner tube 320 is rotated, about its longitudinal axis, with respect to coil 330, the pair of tines $320a_1$ of inner tube 320 transmit the rotation to the entire stack of anchors 100 and advance the entire stack of anchors 100 distally, owing to head threads 114a, 114b of anchors 100 engaging with coil 330.

In accordance with the present disclosure, the components of surgical tacker 200, and anchors 100 are dimensioned such that a single complete and full actuation of trigger 214 results in a firing of a single anchor 100 (e.g., the distal-most anchor of the stack of anchors 100 loaded in endoscopic assembly 300) from endoscopic assembly 300.

With reference to FIGS. 17-22A, two embodiments of follower assemblies are shown and are indicated by reference character 600 (FIGS. 17-20C) and 700 (FIGS. 21-22A). Follower assemblies 600, 700 help ensure that a single complete and full actuation of trigger 214 results in a firing of a single anchor 100 until each anchor 100 has been fired and ejected from surgical tacker 200. Generally, a follower assembly 600, 700 is disposed proximally of a proximal-most anchor 100p (FIGS. 20A-20C) of the stack of anchors 100 and at least partially within inner tube 320. At least a portion of a follower assembly 600, 700 is configured to distally advance along the longitudinal axis of inner tube 320 as inner tube 320 is rotated about the longitudinal axis with respect to handle housing 212. As discussed in further detail below, the distal advancement of either follower assembly 600, 700 helps ensure that the rotation of a proximal portion 320p of inner tube 320 directly corresponds to the rotation of a distal portion 320d of inner tube 320, throughout the ejection of each anchor 100 from surgical tacker 200.

Referring now to FIGS. 17-20C, first embodiment of follower assembly 600 is shown. Follower assembly 600 includes a shaft 610 and a plate 640. Shaft 610 is elongated, includes a head 620 at its distal end, and includes a plurality of indentations 630 along its length. Head 620 of shaft 610 includes head threads 622, 624 which are configured to extend between the pair of tines $320b_1$ of inner tube 320, and which are configured to engage coil 330 in a similar manner to head threads 114a, 114b of anchors 100 engaging coil 330. Indentations 630 of shaft 610 are configured to align with a plurality of fingers 660 of plate 640, as discussed below.

With particular reference to FIGS. 18 and 19, plate 640 of follower assembly 600 is shown. Plate is configured to engage or mate with shaft 610 of follower assembly 600 via a proximal pin (not shown) inserted through respective proximal apertures 610a, 640a of shaft 610 and plate 640, and via a distal pin 642 (FIGS. 20A-20C) inserted through respective distal apertures 610b, 640b of shaft 610 and plate 640. Plate 640 includes an elongated body 650 and a plurality of fingers 660. As shown in FIG. 19, plate 640 has a curved or arcuate profile, which is configured to match the curvature of the profile of shaft 610. In the illustrated embodiments, plurality of fingers 660 includes six fingers 660 spaced apart along the length of elongated body 650; more or fewer fingers 660 are envisioned without departing from the scope of the present disclosure. Fingers 660 are deflectable from elongated body 650, and are biased away from elongated body 650 (e.g., away from shaft 610 when plate 640 is engaged with shaft 610). That is, when shaft 610 and plate 640 are engaged, fingers 660 are deflectable toward corresponding indentations 630 of shaft 610, and are biased away from shaft 610.

In use, follower assembly 600 is positioned within inner tube 320 proximally of proximal-most anchor 100p. Head threads 622, 624 of head 620 of shaft 610 are positioned within or extending through channels $320b_2$ between the pair of tines $320b_1$ of inner tube 320 and in engagement with coil 330 (see FIG. 7). At least some fingers of the plurality of fingers 660 (e.g., all fingers) are positioned proximally of a proximal-most end of the pair of tines $320b_1$, such that the inner wall of inner tube 320 resists the outward bias of fingers 660.

As inner tube 320 is rotated about its longitudinal axis with respect to handle housing 212, the pair of tines $320b_1$ of inner tube 320 transmits the rotation to anchors 100 and head 620 of shaft 610, which thereby advances anchors 100 and follower assembly 600 distally owing to head threads 114a, 114b of anchors 100 and head threads 622, 624 of head 620 engaging with coil 330. As follower assembly 600 advances distally, fingers 660 of plate 640 advance distally, and one finger 660 at a time emerges from proximal portion 320p (FIGS. 20A-20C) of inner tube 320 (disposed proximally of the pair of tines $320b_1$) such that the bias of the fingers 660 is no longer resisted by the inner wall of inner tube 320, which thereby allows portions of fingers 660 to move into channel $320b_2$ between the pair of tines $320b_1$.

The portions of fingers 660 being between the pair of tines $320b_1$ helps ensure the distal portion of the pair of tines $320b_1$ rotates at the same speed or rate as an intermediate portion of the pair of tines $320b_1$ and as a proximal portion of the pair of tines $320b_1$. That is, since the portions of fingers 660 fill (or substantially fill) the gap (or channel $320b_2$) between the pair of tines $320b_1$, it makes it less likely that that distal end of the pair of tines $320b_1$ will be able to rotate with respect to the proximal end of the pair of tines $320b_1$. (When anchors 100 are within inner tube 320, prior to their ejection, the anchors 100 themselves fill the gap between the pair or tines $320b_1$.) Therefore, follower assembly 600 helps ensure that the rotation of proximal portion 320p of inner tube 320 directly corresponds to the rotation of distal portion 320d of inner tube 320, throughout the ejection of each anchor 100 from surgical tacker 200.

Referring now to FIGS. 21-22A, second embodiment of follower assembly 700 is shown. Follower assembly 700 includes a shaft 710, a first ring 760, and a second ring 780. Shaft 710 is elongated, includes a head 720 at its distal end, a proximal portion 740 having a first profile, and a distal portion 750 having a second profile. Head 720 of shaft 710 includes head threads 722, 724 which are configured to extend between the pair of tines $320b_1$ of inner tube 320, and which are configured to engage coil 330 in a similar manner to head threads 114a, 114b of anchors 100 engaging coil 330. Proximal portion 740 of shaft 710 is configured to extend through an aperture 761 of first ring 760, and distal portion 750 of shaft 710 is configured to extend through aperture 761 of first ring 760 and through an aperture 781 of second ring 780.

More particularly, and with reference to FIGS. 21A and 21B, the profile of proximal portion 740 of shaft 710 includes a circular portion 742, a first extension 744, and a second extension 746. In the illustrated embodiment, first extension 744 is radially offset about 60° from second extension 746, but other orientations are encompassed by the present disclosure. The profile of distal portion 750 of shaft 710 includes a circular portion 752, and a first extension 754. As shown in FIGS. 21A and 21B, first extension 754 of distal portion 750 of shaft 710 is radially aligned with first extension 744 of proximal portion 740 of shaft 710.

With particular reference to FIG. 22A, first ring 760 defines an aperture 761 therethrough, and includes a pair of fingers 764. Each finger of the pair of fingers 764 of first ring 760 is configured to extend between the pair of tines $320b_1$ of inner tube 320. Aperture 761 is configured to slidingly engage proximal portion 740 of shaft 710 and distal profile 750 of shaft 710. Aperture 761 includes a similar, yet slightly larger, profile than the profile of proximal portion 740 of shaft 710. In particular, aperture 761 includes a circular portion 762, a first extension 764 and a second extension 766. In the illustrated embodiment, first extension 764 of the profile of first ring 760 is radially offset about 60° from second extension 766 of the profile of first ring 760, but other orientations are encompassed by the present disclosure.

With continued reference to FIG. 22A, second ring 780 defines aperture 781 therethrough, and includes a pair of fingers 784. Each finger of the pair of fingers 784 of second ring 780 is configured to extend between the pair of tines $320b_1$ of inner tube 320. Aperture 781 is configured to slidingly engage distal portion 750 of shaft 710, and is not able to slidingly engage proximal portion 740 of shaft 710. Aperture 781 includes a similar, yet slightly larger, profile than the profile of distal portion 750 of shaft 710. In particular, aperture 781 includes a circular portion 782, and a first extension 784. As shown in FIG. 22A, first extension 784 of the profile of second ring 780 is radially aligned with first extension 764 of the profile of first ring 760.

It is also envisioned that the follower assembly 700 includes additional rings, and additional profiles of shaft 710. For example, a third ring may be disposed proximally of first ring 760, and may slidingly engage a third portion of shaft 710, disposed proximally of proximal portion 740. Here, the aperture of the third ring and the profile of the third portion of shaft 710 may include a circular portion, a first extension, a second extension, and a third extension, where the first and second extensions align with the corresponding extensions of first ring 760.

In use, follower assembly 700 is positioned within inner tube 320 proximally of proximal-most anchor 100p. Head threads 722, 724 of head 720 of shaft 710 are positioned within or extending through channels $320b_2$ between the pair of tines $320b_1$ of inner tube 320 and in engagement with coil 330 (see FIG. 7). First ring 760 is positioned adjacent a proximal end of the pair of tines $320b_1$, second ring 780 is positioned distally of and in contact with or in close proximity to first ring 760, and head 720 of shaft 710 is positioned distally of and in contact with or in close proximity to second ring 780.

As inner tube 320 is rotated about its longitudinal axis with respect to handle housing 212, the pair of tines $320b_1$ of inner tube 320 transmits the rotation to anchors 100 and head 720 of shaft 710, which thereby advances anchors 100 and follower assembly 700 distally owing to head threads 114a, 114b of anchors 100 and head threads 722, 724 of head 720 engaging with coil 330. As follower assembly 700 advances distally, shaft 710 advances distally. Initially, shaft 710 advances distally relative to first ring 760 and second ring 780 due to the relationship between the profile of distal portion 750 of shaft 710 and the aperture 761 of first ring 760 and the aperture 781 of second ring 780.

Upon continued distal advancement of shaft 710 relative to inner tube 320, proximal portion 740 of shaft 710 contacts second ring 780 and pushes second ring 780 distally, as a distal face 746a (FIG. 22) of second extension 746 of proximal portion 740 of shaft 710 contacts a proximal face of second ring 780.

As shown in FIG. 21, fingers 764 of first ring 760 and fingers 784 of second ring 780 are disposed between the pair of tines $320b_1$ (only one finger 764, 784 from first ring 760 and second ring 780 are visible), and distal translation of second ring 780 causes second ring 780 and its fingers 784 to move distally with respect to the pair of tines $320b_1$. The presence of fingers 764, 784 between the pair of tines $320b_1$ helps ensure the distal portion of the pair of tines $320b_1$ rotates at the same speed or rate as an intermediate portion of the pair of tines $320b_1$ and as a proximal portion of the pair of tines $320b_1$. That is, since the fingers 764 of first ring 760 and fingers 784 of second ring 780 fill (or substantially fill) the gap (or channel $320b_2$) between the pair of tines $320b_1$, it makes it less likely that the distal end of the pair of tines $320b_1$ will be able to rotate with respect to the proximal end of the pair of tines $320b_1$. (When anchors 100 are within inner tube 320, prior to their ejection, the anchors 100 themselves fill the gap between the pair or tines $320b_1$.) Therefore, follower assembly 700 helps ensure that the rotation of proximal portion 320p of inner tube 320 directly corresponds to the rotation of distal portion 320d of inner tube 320, throughout the ejection of each anchor 100 from surgical tacker 200.

Surgical tacker 200 may be repeatedly fired to fire anchors from endoscopic assembly 300 until the surgical procedure is complete or until endoscopic assembly 300 is spent of anchors 100. If endoscopic assembly 300 is spent of anchors 100, and if additional anchors 100 are required to complete the surgical procedure, spent endoscopic assembly 300 may be replaced with a new (e.g., loaded with anchors 100) endoscopic assembly 300. Alternatively, is it desired to change the types of anchors 100 that are being used in the surgical procedure, non-spent endoscopic assembly 300 (loaded with a first type of anchors 100) may be replaced with another endoscopic assembly 300 (loaded with a second, different type of anchors 100).

Further details of surgical tacker 200 are described in detail in U.S. patent application Ser. No. 15/129,143 filed on Sep. 26, 2016, and PCT Patent Application Serial No. PCT/CN2014/082675 filed on Jul. 22, 2014, the entire contents of each of which is incorporated by reference herein.

Following a surgical procedure, ferrule 234 may be removed or disconnected from handle housing 212 such that the ferrule 234 and the remainder of handle assembly 210 may by cleaned by sterilization, washing, wiping, autoclaving, chemical processing and the like.

In accordance with the present disclosure, it is also contemplated that handle assembly 210, 210a may be replaced by an electromechanical control module configured and adapted to drive the inner tube of anchor retaining/advancing assembly to fire or actuate the surgical device. The electromechanical control module may include at least one microprocessor, at least one drive motor controllable by the at least one microprocessor, and a source of power for energizing the at least one microprocessor and the at least one drive motor.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A surgical device, comprising:
   a handle housing;
   an endoscopic assembly extending distally from the handle housing and including an inner tube defining a longitudinal axis, the inner tube including a distal portion defining a pair of opposed tines, the endoscopic assembly configured to support a plurality of anchors at least partially therein; and
   a follower assembly disposed at least partially within the inner tube, the follower assembly including a head, a shaft, and a plate disposed in operative engagement with the shaft, a portion of the head is disposed between the pair of opposed tines, the plate including a plurality of longitudinally-spaced fingers,
   wherein actuation of the endoscopic surgical device causes rotation of the inner tube about the longitudinal axis relative to the handle housing, and causes distal advancement of the follower assembly relative to the inner tube.

2. The surgical device according to claim 1, wherein the head of the follower assembly is disposed at a distal end of the shaft.

3. The surgical device according to claim 1, wherein the follower assembly includes a first ring disposed on the shaft, the first ring is longitudinally movable relative to the shaft.

4. The surgical device according to claim 3, wherein a proximal portion of the shaft of the follower assembly includes a first profile, wherein a distal portion of the shaft of the follower assembly includes a second profile, and wherein the first profile is different from the second profile.

5. The surgical device according to claim 4, wherein the first ring is positionable on the distal portion of the shaft and is physically prevented from being positioned on the proximal portion of the shaft.

6. The surgical device according to claim 4, wherein after a predetermined amount of longitudinal movement of the shaft of the follower assembly relative to the inner tube, the proximal portion of the shaft forces the first ring distally relative to the inner tube.

7. The surgical device according to claim 4, wherein the follower assembly includes a second ring disposed on the shaft, the second ring is longitudinally movable relative to the shaft.

8. The surgical device according to claim 7, wherein the second ring is positionable on the distal portion of the shaft and on the proximal portion of the shaft.

9. The surgical device according to claim 7, wherein the first ring defines a first aperture, wherein the second ring defines a second aperture, and wherein the first aperture has a different profile than the second aperture.

10. The surgical device according to claim 1, wherein each finger of the plurality of fingers of the plate of the follower assembly is biased away from the shaft.

11. The surgical device according to claim 1, wherein the follower assembly is movable between a first position where at least one finger of the plurality of fingers is positioned proximally of the pair of opposed tines and a second position where the at least one finger of the plurality of fingers is positioned distally of the pair of opposed tines.

12. The surgical device according to claim 11, wherein when the follower assembly is in the second position, part of the at least one finger positioned distally of the pair of opposed tines is positioned between the pair of opposed tines.

13. The surgical device according to claim 1, further comprising a coil disposed within the inner tube.

14. The surgical device according to claim 13, wherein the head of the follower assembly is disposed in operative engagement with the coil.

15. The surgical device according to claim 14, wherein the follower assembly is longitudinally movable relative to the coil.

16. The surgical device according to claim 1, further comprising a plurality of anchors disposed at least partially within the endoscopic assembly and disposed distally of the head of the follower assembly.

17. A surgical device, comprising:
a handle housing;
an endoscopic assembly extending distally from the handle housing and including an inner tube defining a longitudinal axis, the inner tube including a distal portion defining a pair of opposed tines, the endoscopic assembly configured to support a plurality of anchors at least partially therein; and
a follower assembly disposed at least partially within the inner tube, the follower assembly including a head, a shaft, a first ring disposed on the shaft, and a second ring disposed on the shaft, wherein a portion of the head is disposed between the pair of opposed tines, wherein the first ring includes a pair of fingers, each finger of the pair of fingers of the first ring extends between the pair of opposed tines of the inner tube, wherein the second ring includes a pair of fingers, each finger of the pair of fingers of the second ring extends between the pair of opposed tines of the inner tube, and wherein the first ring and the second ring are longitudinally movable relative to the shaft, and wherein the second ring is longitudinally movable relative to the first ring,
wherein actuation of the endoscopic surgical device causes rotation of the inner tube about the longitudinal axis relative to the handle housing, and causes distal advancement of at least a portion of the follower assembly relative to the inner tube.

18. The surgical device according to claim 17, wherein the first ring defines a first aperture, wherein the second ring defines a second aperture, and wherein the first aperture has a different profile than the second aperture.

19. The surgical device according to claim 17, wherein the first ring is positionable on a distal portion of the shaft and is physically prevented from being positioned on a proximal portion of the shaft, and wherein the second ring is positionable on the distal portion of the shaft and on the proximal portion of the shaft.

20. The surgical device according to claim 19, wherein after a predetermined amount of longitudinal movement of the shaft of the follower assembly relative to the inner tube, the proximal portion of the shaft forces the first ring distally relative to the inner tube.

* * * * *